(12) United States Patent
Bollen et al.

(10) Patent No.: US 7,173,117 B2
(45) Date of Patent: Feb. 6, 2007

(54) **CODON OPTIMISED RECOMBINANT *DERMAPHAGOIDES* ALLERGENS**

(75) Inventors: Alex Bollen, Gosselies (BE); Paul Jacobs, Brussels (BE); Alain Jacquet, Gosselies (BE); Marc Georges Francis Massaer, Brussels (BE)

(73) Assignee: GlaxoSmithKline Biologicals S.A., Rixensart (BE)

( * ) Notice: Subject to any disclaimer, the term of this patent is extended or adjusted under 35 U.S.C. 154(b) by 645 days.

(21) Appl. No.: 10/297,563

(22) PCT Filed: Jun. 7, 2001

(86) PCT No.: PCT/EP01/06483

§ 371 (c)(1), (2), (4) Date: Dec. 9, 2002

(87) PCT Pub. No.: WO01/96385

PCT Pub. Date: Dec. 20, 2001

(65) Prior Publication Data

US 2003/0138441 A1    Jul. 24, 2003

(30) Foreign Application Priority Data

Jun. 10, 2000    (GB) .................................. 0014288.5

(51) Int. Cl.
| | |
|---|---|
| C07H 21/04 | (2006.01) |
| C12N 15/00 | (2006.01) |
| C12N 15/02 | (2006.01) |
| C12P 21/04 | (2006.01) |
| G01N 33/53 | (2006.01) |

(52) U.S. Cl. ................. 536/23.1; 536/23.2; 435/320.1; 435/325; 435/70.1

(58) Field of Classification Search .................... None
See application file for complete search history.

(56) References Cited

U.S. PATENT DOCUMENTS 5,433,948 A * 7/1995 Thomas et al. .......... 424/185.1
5,670,367 A * 9/1997 Dorner et al. ........... 435/320.1
6,455,686 B1 * 9/2002 McCall et al. ............. 536/23.4

FOREIGN PATENT DOCUMENTS

| WO | WO 97/31115 | 8/1997 |
|---|---|---|
| WO | WO 99/25823 | 5/1999 |

OTHER PUBLICATIONS

Andre et al., "Increased Immune Response Elicited by DNA Vaccination with a Synthetic GP120 Sequence with Optimized Codon Usage", *Journal of Virology*, 72(2): 1497-1503 (1998).

Yang et al., "Optimized Codon Usage and Chromophore Mutations Provide Enhanced Sensitivity with the Green Fluorescent Protein", *Nucleic Acids Research*, 24(22): 4592-4593 (1996).

Kim et al., "Codon Optimization for High-Level Expression of Human Erythropoietin (EPO) in Mammalian Cells", *Gene: an International Journal on Genes and Genomes*, 199(1-2): 293-301 (1997).

Kawamoto et al., "Cloning and Expression of Der f 6, A Serine Protease Allergen from the House Dust Mite, Dermatophagoides Farinae", *Biochimica et Biophysica Acta*, 1454(2): 201-207 (1999).

Hale, et al., *Protein Expression and Purification*, vol. 12 pp. 185-188 (1998).

* cited by examiner

*Primary Examiner*—Daniel M. Sullivan
*Assistant Examiner*—Laura McGillem
(74) *Attorney, Agent, or Firm*—Jason C. Fedon; Edward R. Gimmi; Charles M. Kinzig

(57) ABSTRACT

The present invention relates to codon optimised polynucleotides which are efficiently expressed in mammalian cells and encode insect proteins from *Dermaphagoids* dust mite. In particular, the optimised codon polynucleotides encode a protein from *Dermaphagoides pteronyssinus*, such as DerP1 or proDerP1. The present invention also provides methods of preparing pharmaceutical compositions comprising the expression of the codon optimised polynucleotides, and vectors and transformed host cells comprising them.

4 Claims, 8 Drawing Sheets

Figure 2:
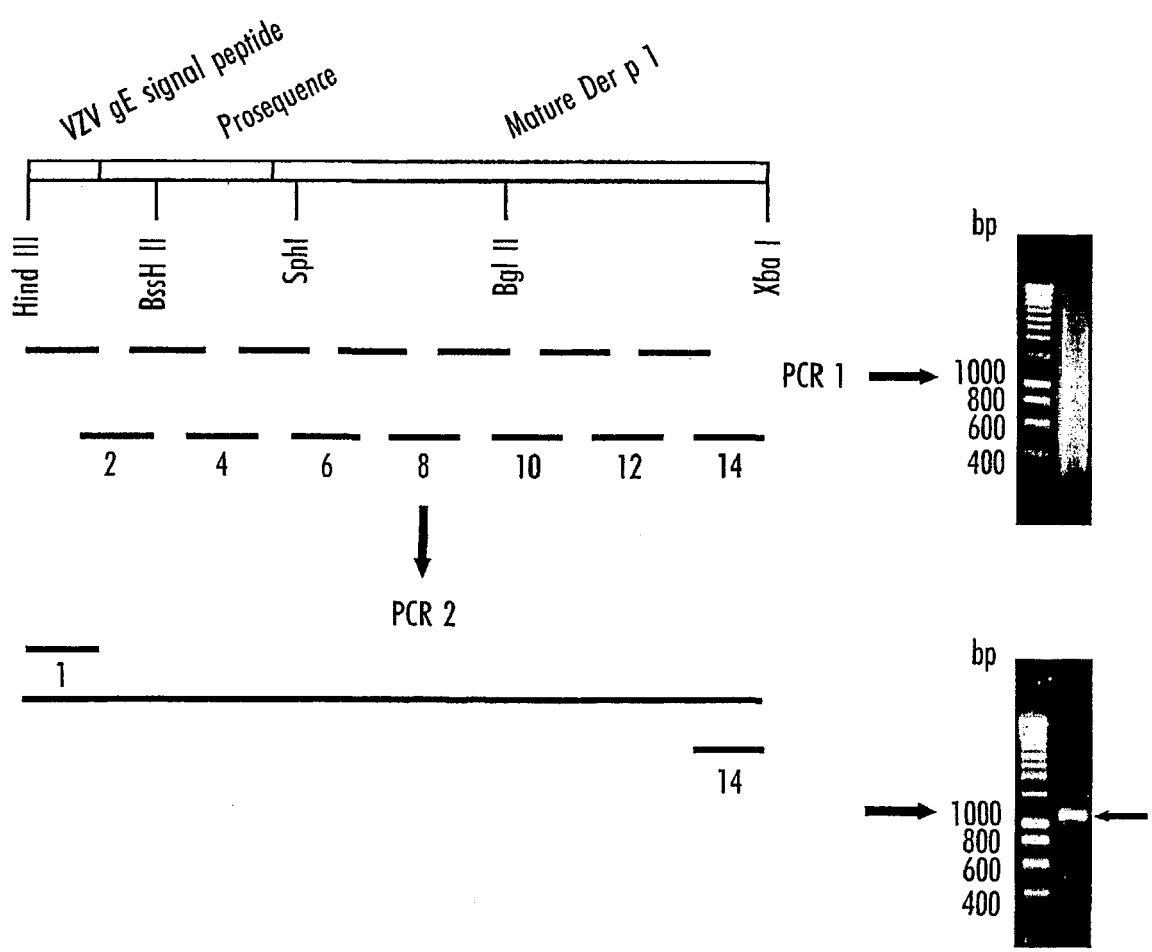

FIG 1.

Ala
| GC | High | ProDer p 1 | Synthetic |
|---|---|---|---|
| G | 17 | 0 | 20 |
| A | 13 | 21 | 11 |
| T | 17 | 53 | 20 |
| C | 53 | 26 | 49 |

Arg
| | | High | ProDer p 1 | Synthetic |
|---|---|---|---|---|
| AG | G | 18 | 0 | 20 |
| | A | 10 | 0 | 11 |
| CG | G | 21 | 0 | 22 |
| | A | 6 | 50 | 6 |
| | T | 7 | 44 | 6 |
| | C | 37 | 6 | 39 |

Asn
| AA | High | ProDer p 1 | Synthetic |
|---|---|---|---|
| T | 22 | 48 | 26 |
| C | 78 | 52 | 74 |

Asp
| GA | High | ProDer p 1 | Synthetic |
|---|---|---|---|
| T | 25 | 94 | 25 |
| C | 75 | 6 | 75 |

Cys
| TG | High | ProDer p 1 | Synthetic |
|---|---|---|---|
| T | 32 | 57 | 29 |
| C | 68 | 43 | 71 |

Gln
| CA | High | ProDer p 1 | Synthetic |
|---|---|---|---|
| G | 88 | 0 | 88 |
| A | 12 | 100 | 12 |

Glu
| GA | High | ProDer p 1 | Synthetic |
|---|---|---|---|
| G | 75 | 0 | 75 |
| A | 25 | 100 | 25 |

Gly
| GG | High | ProDer p 1 | Synthetic |
|---|---|---|---|
| G | 24 | 0 | 25 |
| A | 14 | 15 | 15 |
| T | 12 | 70 | 10 |
| C | 50 | 15 | 50 |

His
| CA | High | ProDer p 1 | Synthetic |
|---|---|---|---|
| T | 21 | 50 | 25 |
| C | 79 | 50 | 75 |

Ile
| AT | High | ProDer p 1 | Synthetic |
|---|---|---|---|
| A | 5 | 0 | 4 |
| T | 18 | 54 | 17 |
| C | 77 | 46 | 79 |

Leu
| | | High | ProDer p 1 | Synthetic |
|---|---|---|---|---|
| TT | G | 6 | 75 | 5 |
| | A | 2 | 10 | 5 |
| CT | G | 58 | 0 | 60 |
| | A | 3 | 0 | 0 |
| | T | 5 | 5 | 5 |
| | C | 26 | 10 | 25 |

Lys
| AA | High | ProDer p 1 | Synthetic |
|---|---|---|---|
| G | 82 | 0 | 82 |
| A | 18 | 100 | 18 |

Phe
| TT | High | ProDer p 1 | Synthetic |
|---|---|---|---|
| T | 20 | 42 | 17 |
| C | 80 | 58 | 83 |

Pro
| CC | High | ProDer p 1 | Synthetic |
|---|---|---|---|
| G | 17 | 0 | 22 |
| A | 16 | 89 | 11 |
| T | 19 | 0 | 22 |
| C | 48 | 11 | 44 |

Ser
| | | High | ProDer p 1 | Synthetic |
|---|---|---|---|---|
| AG | T | 10 | 23 | 9 |
| | C | 34 | 14 | 41 |
| TC | G | 9 | 9 | 9 |
| | A | 5 | 41 | 5 |
| | T | 13 | 5 | 9 |
| | C | 28 | 9 | 27 |

Thr
| AC | High | ProDer p 1 | Synthetic |
|---|---|---|---|
| G | 15 | 0 | 18 |
| A | 14 | 9 | 18 |
| T | 14 | 55 | 18 |
| C | 57 | 36 | 45 |

Tyr
| TA | High | ProDer p 1 | Synthetic |
|---|---|---|---|
| T | 36 | 57 | 29 |
| C | 74 | 43 | 71 |

Val
| GT | High | ProDer p 1 | Synthetic |
|---|---|---|---|
| G | 64 | 0 | 65 |
| A | 5 | 17 | 6 |
| T | 7 | 39 | 6 |
| C | 25 | 44 | 24 |

Fig. 4
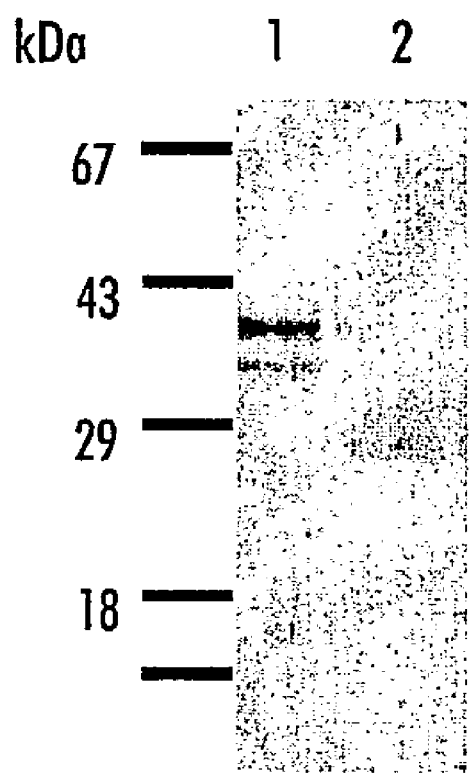
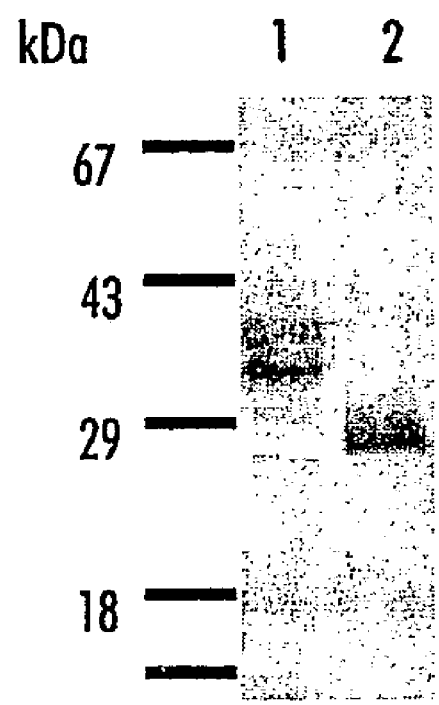
A
B

SEQUENCE LISTING

```
<160> NUMBER OF SEQ ID NOS: 17

<210> SEQ ID NO 1
<211> LENGTH: 114
<212> TYPE: DNA
<213> ORGANISM: Artificial Sequence
<220> FEATURE:
<223> OTHER INFORMATION: Codon Optimised Dermaphagoides gene

<400> SEQUENCE: 1
gaagcttcgg gcgaattgcg tggtttttaag tgactatatt cgagggtcgc ctgtaatatg       60
gggacagtta ataaacctgt ggtgggggta ttgatggggt tcggaattat cacg            114

<210> SEQ ID NO 2
<211> LENGTH: 96
<212> TYPE: DNA
<213> ORGANISM: Artificial Sequence
<220> FEATURE:
<223> OTHER INFORMATION: Codon Optimised Dermaphagoides gene

<400> SEQUENCE: 2
gaaggctttc ttgtattcct cgaaggtctt aatggagctc ggccgtgctc tgaccggatt       60
cgttatacgc aaggtacccg tgataattcc gaaccc                                  96

<210> SEQ ID NO 3
<211> LENGTH: 97
<212> TYPE: DNA
<213> ORGANISM: Artificial Sequence
<220> FEATURE:
<223> OTHER INFORMATION: Codon Optimised Dermaphagoides gene

<400> SEQUENCE: 3
ggaatacaag aaagccttca acaagagcta tgccaccttc gaggacgagg aggccgcgcg       60
caagaacttc ctggaaagcg tgaaatacgt gcagagc                                 97

<210> SEQ ID NO 4
<211> LENGTH: 113
<212> TYPE: DNA
<213> ORGANISM: Artificial Sequence
<220> FEATURE:
<223> OTHER INFORMATION: Codon Optimised Dermaphagoides gene

<400> SEQUENCE: 4
```

```
gtcttaaggt gttcgaaagc ctcggcgctc atcaggaacc ggttcttgaa ctcgtctaaa      60
gacaggtcgg acaggtgatt tatagccccg ccgttgctct gcacgtattt cac            113

<210> SEQ ID NO 5
<211> LENGTH: 93
<212> TYPE: DNA
<213> ORGANISM: Artificial Sequence
<220> FEATURE:
<223> OTHER INFORMATION: Codon Optimised Dermaphagoides gene

<400> SEQUENCE: 5
ctttcgaaca ccttaagacc cagtttgatc tcaacgcgga gaccaacgcc tgcagtatca      60
acggcaatgc ccccgctgag attgatctgc gcc                                  93

<210> SEQ ID NO 6
<211> LENGTH: 100
<212> TYPE: DNA
<213> ORGANISM: Artificial Sequence
<220> FEATURE:
<223> OTHER INFORMATION: Codon Optimised Dermaphagoides gene

<400> SEQUENCE: 6
gactctgtcg cggccacgcc tgaaaaggcc caacaagacc cgcagccgcc ttgcatgcgg      60
atgggagtca cggtcctcat ctggcgcaga tcaatctcag                           100

<210> SEQ ID NO 7
<211> LENGTH: 92
<212> TYPE: DNA
<213> ORGANISM: Artificial Sequence
<220> FEATURE:
<223> OTHER INFORMATION: Codon Optimised Dermaphagoides gene

<400> SEQUENCE: 7
gtggccgcga cagagtcggc ataccctcgcg tatcggaatc agagcctgga cctcgctgag     60
caggagctcg ttgactgcgc ctcccaacac gg                                   92

<210> SEQ ID NO 8
<211> LENGTH: 100
<212> TYPE: DNA
<213> ORGANISM: Artificial Sequence
<220> FEATURE:
<223> OTHER INFORMATION: Codon Optimised Dermaphagoides gene

<400> SEQUENCE: 8
gctacgtatc ggtaatagct ttcctgcacg acgccattat gctggatgta ttcgatacct      60
ctgggaatcg tatccccatg acatccgtgt tgggaggcgc                           100

<210> SEQ ID NO 9
<211> LENGTH: 87
<212> TYPE: DNA
<213> ORGANISM: Artificial Sequence
<220> FEATURE:
<223> OTHER INFORMATION: Codon Optimised Dermaphagoides gene

<400> SEQUENCE: 9
gctattaccg atacgtagct agggagcagt cctgccgccg tcctaacgca cagcgcttcg      60
gcatttccaa ttattgccag atctacc                                         87

<210> SEQ ID NO 10
<211> LENGTH: 95
<212> TYPE: DNA
```

<213> ORGANISM: Artificial Sequence
<220> FEATURE:
<223> OTHER INFORMATION: Codon Optimised Dermaphagoides gene

<400> SEQUENCE: 10

| ccttgattcc gatgatgaca gcgatggcgc tgtgcgtctg cgccagggcc tccctgatct | 60 |
| tgttggcatt agggggtag atctggcaat aattg | 95 |

<210> SEQ ID NO 11
<211> LENGTH: 91
<212> TYPE: DNA
<213> ORGANISM: Artificial Sequence
<220> FEATURE:
<223> OTHER INFORMATION: Codon Optimised Dermaphagoides gene

<400> SEQUENCE: 11

| gtcatcatcg gaatcaagga tctggacgca ttccggcact atgacgggcg cacaatcatc | 60 |
| cagcgcgaca acggatatca gccaaactac c | 91 |

<210> SEQ ID NO 12
<211> LENGTH: 66
<212> TYPE: DNA
<213> ORGANISM: Artificial Sequence
<220> FEATURE:
<223> OTHER INFORMATION: Codon Optimised Dermaphagoides gene

<400> SEQUENCE: 12

| gtagtccacc ccctgggcgt tcgagtaacc cacgatgttg accgcgtggt agtttggctg | 60 |
| atatcc | 66 |

<210> SEQ ID NO 13
<211> LENGTH: 82
<212> TYPE: DNA
<213> ORGANISM: Artificial Sequence
<220> FEATURE:
<223> OTHER INFORMATION: Codon Optimised Dermaphagoides gene

<400> SEQUENCE: 13

| ccagggggtg gactactgga tcgtgagaaa cagttgggac actaactggg gcgacaacgg | 60 |
| ctacggctac ttcgccgcca ac | 82 |

<210> SEQ ID NO 14
<211> LENGTH: 85
<212> TYPE: DNA
<213> ORGANISM: Artificial Sequence
<220> FEATURE:
<223> OTHER INFORMATION: Codon Optimised Dermaphagoides gene

<400> SEQUENCE: 14

| gctctagact cgagggatcc ttacaggatc accacgtacg ggtactcctc gatcatcatc | 60 |
| aggtcgatgt tggcggcgaa gtagc | 85 |

<210> SEQ ID NO 15
<211> LENGTH: 909
<212> TYPE: DNA
<213> ORGANISM: Dermaphagoides pteronyssinus

<400> SEQUENCE: 15

| cgtccatcat cgatcaaaac ttttgaagaa tacaaaaaag ccttcaacaa agttatgct | 60 |
| accttcgaag atgaagaagc tgcccgtaaa aacttttttgg aatcagtaaa atatgttcaa | 120 |
| tcaaatggag gtgccatcaa ccatttgtcc gatttgtcgt tggatgaatt caaaaaccga | 180 |

-continued

```
tttttgatga gtgcagaagc ttttgaacac ctcaaaactc aattcgattt gaatgctgaa      240
actaacgcct gcagtatcaa tggaaatgct ccagctgaaa tcgatttgcg acaaatgcga      300
actgtcactc ccattcgtat gcaaggaggc tgtggttcat gttgggcttt ctctggtgtt      360
gccgcaactg aatcagctta tttggcttac cgtaatcaat cattggatct tgctgaacaa      420
gaattagtcg attgtgcttc ccaacacggt tgtcatggtg ataccattcc acgtggtatt      480
gaatacatcc aacataatgg tgtcgtccaa gaaagctact atcgatacgt tgcacgagaa      540
caatcatgcc gacgaccaaa tgcacaacgt ttcggtatct caaactattg ccaaatttac      600
ccaccaaatg taaacaaaat tcgtgaagct ttggctcaaa cccacagcgc tattgccgtc      660
attattggca tcaaagattt agacgcattc cgtcattatg atggccgaac aatcattcaa      720
cgcgataatg gttaccaacc aaactatcac gctgtcaaca ttgttggtta cagtaacgca      780
caaggtgtcg attattggat cgtacgaaac agttgggata ccaattgggg tgataatggt      840
tacggttatt ttgctgccaa catcgatttg atgatgattg aagaatatcc atatgttgtc      900
attctctaa                                                              909
```

<210> SEQ ID NO 16
<211> LENGTH: 1511
<212> TYPE: DNA
<213> ORGANISM: Artificial Sequence
<220> FEATURE:
<221> NAME/KEY: CDS
<222> LOCATION: (1)...(909)
<223> OTHER INFORMATION: Codon Optimised Dermaphagoides gene
<221> NAME/KEY: misc_feature
<222> LOCATION: 79, 160, 225, 230, 239, 308, 384, 391, 449, 459, 464,
    527, 548, 697, 699, 711, 775, 852, 857, 865, 940, 955, 959, 1018,
    1026, 1034, 1039, 1101, 1194, 1250, 1257, 1261, 1273, 1333,
    1337, 1356, 1416, 1425, 1443
<223> OTHER INFORMATION: n = A,T,C or G
<220> FEATURE:
<221> NAME/KEY: misc_feature
<222> LOCATION: 79, 160, 225, 230, 239, 308, 384, 391, 449, 459, 464,
    527, 548, 697, 699, 711, 775, 852, 857, 865, 940, 955, 959, 1018,
    1026, 1034, 1039, 1101, 1194, 1250, 1257, 1261, 1273, 1333,
    1337, 1356, 1416, 1425, 1443
<223> OTHER INFORMATION: Codon Optimised Dermaphagoides gene
<220> FEATURE:
<223> OTHER INFORMATION: n = A,T,C or G

<400> SEQUENCE: 16

```
cgg ccg agc tcc att aag acc ttc gag gaa tac aag aaa gcc ttc aac       48
Arg Pro Ser Ser Ile Lys Thr Phe Glu Glu Tyr Lys Lys Ala Phe Asn
 1               5                  10                  15 arg rsr sry sth rhg ugu tyr ysy saa has naa gag cta tgc cac ctt       96
Xaa Xaa Xaa Xaa Xaa Cys Xaa Xaa Xaa Xaa Xaa Glu Leu Cys His Leu
                20                  25                  30 cga gga cga gga ggc cgc gcg caa gaa ctt cys srt yra ath rhg uas      144
Arg Gly Arg Gly Gly Arg Ala Gln Glu Leu Xaa Xaa Xaa Ile Xaa Xaa
            35                  40                  45 gug uaa aaa rgy sas nhc tgg aaa gcg tga aat acg tgc aga gca acg      192
Val  *  Lys Xaa Xaa Xaa Trp Lys Ala  *  Asn Thr Cys Arg Ala Thr
        50                  55                  60 gcg ggg cta taa atc acu gus rva yst yrv agn sra sng ygy aaa snh      240
Ala Gly Leu  *  Ile Thr Xaa Xaa Xaa Xaa Xaa Xaa Xaa Xaa Lys Xaa
        65                  70                  75 sct gtc cga cct gtc ttt aga cga gtt caa gaa ccg gtt cct gat gag      288
Xaa Val Arg Pro Val Phe Arg Arg Val Gln Glu Pro Val Pro Asp Glu
        80                  85                  90 cus ras usr uas guh ysa sna rgh umt srg ccg agg ctt tcg aac acc      336
```

| | | | | | | | | | | | | | | | |
|---|---|---|---|---|---|---|---|---|---|---|---|---|---|---|---|
| Xaa | Xaa | Xaa | Xaa | Xaa | Xaa | Xaa | Xaa | Xaa | Xaa | Pro | Arg | Leu | Ser | Asn | Thr |
| | | 95 | | | | | 100 | | | | 105 | | | | |

```
tta aga ccc agt ttg atc tca acg cgg aga agu aah guh suy sth rgn      384
Leu Arg Pro Ser Leu Ile Ser Thr Arg Arg Ser Xaa Xaa Xaa Xaa Xaa
110             115                 120                 125 has uas naa gua cca acg cct gca gta tca acg gca atg ccc ccg ctg      432
Xaa Xaa Xaa Val Pro Thr Pro Ala Val Ser Thr Ala Met Pro Pro Leu
                130                 135                 140 aga ttg atc tgt hra sna acy ssr asn gya sna ara agu asu cgc cag      480
Arg Leu Ile Cys Xaa Xaa Xaa Xaa Xaa Xaa Xaa Xaa Ser Xaa Arg Gln
                145                 150                 155 atg agg acc gtg act ccc atc cgc atg caa ggc ggc tgc ggg arg gnm      528
Met Arg Thr Val Thr Pro Ile Arg Met Gln Gly Gly Cys Gly Xaa Xaa
            160                 165                 170 tar gth rva thr rar gmt gng ygy cys gyt ctt gtt ggg cct ttt cag      576
Xaa Xaa Xaa Xaa Xaa Xaa Xaa Xaa Xaa Xaa Leu Val Gly Pro Phe Gln
            175                 180                 185 gcg tgg ccg cga cag agt cgg cat acc tcs rcy str aah srg yva aaa      624
Ala Trp Pro Arg Gln Ser Arg His Thr Xaa Xaa Xaa Xaa Xaa Xaa Lys
190             195                 200                 205 ath rgu sra aty rug cgt atc gga atc aga gcc tgg acc tcg ctg agc      672
Ile Xaa Xaa Xaa Xaa Arg Ile Gly Ile Arg Ala Trp Thr Ser Leu Ser
                210                 215                 220 agg agc tcg ttg aca aty rar gas ngn sru asu aag ugn guu vaa stg      720
Arg Ser Ser Leu Thr Xaa Xaa Xaa Xaa Xaa Xaa Lys Xaa Val Xaa Xaa
                225                 230                 235 cgc ctc cca aca cgg atg tca tgg gga tac gat tcc cag agg tat ccy      768
Arg Leu Pro Thr Arg Met Ser Trp Gly Tyr Asp Ser Gln Arg Tyr Xaa
            240                 245                 250 saa srg nhs gyc ysh sgy ast hrr arg gyg aat aca tcc agc ata atg      816
Xaa Xaa Xaa Xaa Xaa Xaa Xaa Xaa Xaa Asn Thr Ser Ser Ile Met
        255                 260                 265 gcg tcg tgc agg aaa gct att acc gat acg uty rgn hsa sng yva vag      864
Ala Ser Cys Arg Lys Ala Ile Thr Asp Thr Xaa Xaa Xaa Xaa Xaa Xaa
270             275                 280                 285 ngu srt yrt yra rgt yrg tag cta ggg agc agt cct gcc gcc gtc          909
Xaa Xaa Xaa Xaa Xaa Xaa  *  Leu Gly Ser Ser Pro Ala Ala Val
                290                 295 ctaacgcaca gcgcttcggc vaaaarggug nsrcysarga rgrasnaagn arghgyattt   969
ccaattattg ccagatctac ccccctaatg ccaacaagat caggsrasnt yrcysgntyr   1029
rrasnaaasn ysarggaggc cctggcgcag acgcacagcg ccatcgctgt catcatcgga   1089
atcguaauaa gnthrhssra aaavagyaag gatctggacg cattccggca ctatgacggg   1149
cgcacaatca tccagysasu asaaharghs tyrasgyarg thrgncgcga caacggatat   1209
cagccaaact accacgcggt caacatcgtg ggtargasas ngytyrgnra sntyrhsaav   1269
aasnvagyta ctcgaacgcc caggggtgg actactggat cgtgagaaac agttggtyrs   1329
rasnaagngy vaastyrtrv aargasnsrt rgacactaac tggggcgaca acggctacgg   1389
ctacttcgcc gccaacatca sthrasntrg yasasngyty rgytyrhaaa aasngacctg   1449
atgatgatcg aggagtaccc gtacgtggtg atcctgtaaa sumtmtgugu tyrrtyrvav   1509
au                                                                   1511
```

<210> SEQ ID NO 17
<211> LENGTH: 299
<212> TYPE: PRT
<213> ORGANISM: Artificial Sequence
<220> FEATURE:

-continued

```
<221> NAME/KEY: VARIANT
<222> LOCATION: 17, 18, 19, 20, 21, 23, 24, 25, 26, 27, 43, 44, 45, 47,
      48, 51, 52, 53, 68, 69, 70, 71, 72, 73, 74, 75, 77, 78, 94,
      95, 96, 97, 98, 99, 100, 101, 102, 103, 121, 122, 123, 124,
      125, 126, 127, 128, 146, 147, 148, 149, 150, 151, 152
<223> OTHER INFORMATION: Xaa = Any Amino Acid
<220> FEATURE:
<221> NAME/KEY: VARIANT
<222> LOCATION: 153, 155, 172, 173, 174, 175, 176, 177, 178, 179, 180,
      181, 182, 183, 199, 200, 201, 202, 203, 204, 207, 208, 209, 210,
      227, 228, 229, 230, 231, 232, 234, 236, 237, 253, 254, 255,
      256, 257, 258, 259, 260, 261, 262, 263, 280, 281, 282
<223> OTHER INFORMATION: Xaa = Any Amino Acid
<221> NAME/KEY: VARIANT
<222> LOCATION: 283, 284, 285, 286, 287, 288, 289, 290, 291
<223> OTHER INFORMATION: Xaa = Any Amino Acid
<220> FEATURE:
<221> NAME/KEY: VARIANT
<222> LOCATION: 17, 18, 19, 20, 21, 23, 24, 25, 26, 27, 43, 44, 45, 47,
      48, 51, 52, 53, 68, 69, 70, 71, 72, 73, 74, 75, 77, 78, 94,
      95, 96, 97, 98, 99, 100, 101, 102, 103, 121, 122, 123, 124,
      125, 126, 127, 128, 146, 147, 148, 149, 150, 151, 152
<223> OTHER INFORMATION: Codon Optimised Dermaphagoides gene
<220> FEATURE:
<221> NAME/KEY: VARIANT
<222> LOCATION: 153, 155, 172, 173, 174, 175, 176, 177, 178, 179, 180,
      181, 182, 183, 199, 200, 201, 202, 203, 204, 207, 208, 209, 210,
      227, 228, 229, 230, 231, 232, 234, 236, 237, 253, 254, 255,
      256, 257, 258, 259, 260, 261, 262, 263, 280, 281, 282
<223> OTHER INFORMATION: Xaa = Any Amino Acid
<220> FEATURE:
<223> OTHER INFORMATION: Xaa = Any Amino Acid

<400> SEQUENCE: 17

Arg Pro Ser Ser Ile Lys Thr Phe Glu Glu Tyr Lys Lys Ala Phe Asn
  1               5                  10                  15

Xaa Xaa Xaa Xaa Xaa Cys Xaa Xaa Xaa Xaa Xaa Glu Leu Cys His Leu
             20                  25                  30

Arg Gly Arg Gly Gly Arg Ala Gln Glu Leu Xaa Xaa Xaa Ile Xaa Xaa
         35                  40                  45

Val Lys Xaa Xaa Xaa Trp Lys Ala Asn Thr Cys Arg Ala Thr Ala Gly
 50                  55                  60

Leu Ile Thr Xaa Xaa Xaa Xaa Xaa Xaa Xaa Lys Xaa Xaa Val Arg
 65                  70                  75                  80

Pro Val Phe Arg Arg Val Gln Glu Pro Val Pro Asp Glu Xaa Xaa Xaa
                 85                  90                  95

Xaa Xaa Xaa Xaa Xaa Xaa Xaa Pro Arg Leu Ser Asn Thr Leu Arg Pro
            100                 105                 110

Ser Leu Ile Ser Thr Arg Arg Ser Xaa Xaa Xaa Xaa Xaa Xaa Xaa Xaa
            115                 120                 125

Val Pro Thr Pro Ala Val Ser Thr Ala Met Pro Pro Leu Arg Leu Ile
            130                 135                 140

Cys Xaa Xaa Xaa Xaa Xaa Xaa Xaa Ser Xaa Arg Gln Met Arg Thr
145                 150                 155                 160

Val Thr Pro Ile Arg Met Gln Gly Gly Cys Gly Xaa Xaa Xaa Xaa
                165                 170                 175

Xaa Xaa Xaa Xaa Xaa Xaa Xaa Leu Val Gly Pro Phe Gln Ala Trp Pro
            180                 185                 190

Arg Gln Ser Arg His Thr Xaa Xaa Xaa Xaa Xaa Xaa Lys Ile Xaa Xaa
            195                 200                 205

Xaa Xaa Arg Ile Gly Ile Arg Ala Trp Thr Ser Leu Ser Arg Ser Ser
        210                 215                 220

Leu Thr Xaa Xaa Xaa Xaa Xaa Xaa Lys Xaa Val Xaa Xaa Arg Leu Pro
225                 230                 235                 240
```

-continued

```
Thr Arg Met Ser Trp Gly Tyr Asp Ser Gln Arg Tyr Xaa Xaa Xaa Xaa
                245                 250                 255

Xaa Xaa Xaa Xaa Xaa Xaa Xaa Asn Thr Ser Ser Ile Met Ala Ser Cys
            260                 265                 270

Arg Lys Ala Ile Thr Asp Thr Xaa Xaa Xaa Xaa Xaa Xaa Xaa Xaa Xaa
        275                 280                 285

Xaa Xaa Xaa Leu Gly Ser Ser Pro Ala Ala Val
    290                 295
```

CODON OPTIMISED RECOMBINANT *DERMAPHAGOIDES* ALLERGENS

The present invention relates to codon optimised polynucleotides which are efficiently expressed in mammalian cells and encode insect proteins from *Dermaphagoides* dust mite. In particular, the optimised codon polynucleotides encode a protein from *Dermaphagoides pteronyssinus*, such as DerP1 or proDerP1. The present invention also provides methods of preparing pharmaceutical compositions comprising the expression of the codon optimised polynucleotides, and vectors and transformed host cells comprising them.

The allergens from the house dust mite *Dermatophagoides* have long been recognised to be associated with allergic hypersensitivity reactions such as asthma [1]. Amongst these molecules, Der p 1 is an immunodominant allergen which elicits the strongest IgE-mediated immune response [2,3]. The cysteine proteinase activity of Der p 1 was shown to amplify its potent allergenicity [4,5]. The Der p 1 encoding cDNA sequence reveals that, like many mammalian and plant proteinases, Der p 1 is synthetised as an inactive preproenzyme of 320 amino acid residues which is subsequently processed into a 222-amino acid mature form [6,7]. The maturation of ProDer p 1 is not known to date but it is thought that the allergen is processed by the cleavage of the 80-residues proregion.

Mature Der p 1 was successfully purified from the whole house dust mite culture but with weak overall yield [8]. Recombinant production of allergens represents an efficient way to obtain defined materials with high yields for a variety of experimental procedures such as immunological studies, diagnosis, treatment of IgE-mediated allergic disorders by immunotherapy and understanding structure-function relationships [9]. Previous attempts of Der p 1 expression in bacteria and yeast indicated that the allergen was poorly expressed and mainly under an insoluble form [10–12]. Moreover, recombinant Der p 1 produced in bacteria was shown to have weak IgE binding activity. The recombinant protein expressed in yeast was recognized by specific IgE at, however, a lower level than the natural protein.

Recombinant DerP 1 allergens with reduced enzymatic activity that are encoded by the native non-optimised *Dermaphagoides* gene are described in WO 99/25823. Other recombinant *Dermaphagoides* allergens include DerP1 (U.S. Pat. No. 6,077,518), DerPII (U.S. Pat. No. 6,132,734), and DerFI and DerFII (U.S. Pat. Nos. 5,973,132; 5,958,415; 5,876,722).

It is clearly desirable to enable the efficient expression of recombinant *Dermaphagoides* allergens for use in the manufacture of pharmaceuticals, vaccines or diagnostic assays. It is furthermore desirable for the expression systems to produce recombinant allergen at high levels that is also in the same conformation and immunological properties as native *Dermaphagoides* allergens.

The present invention achieves such advantages by providing a polynucleotide sequence which encodes a *Dermaphagoides* protein, wherein the codon usage pattern of the polynucleotide sequence is altered to resemble that of highly expressed mammalian genes. Accordingly, the cloning and expression of recProDer p 1 has been achieved in Chinese Hamster Ovary cells (CHO) with high efficiency and produces a product which displayed very similar IgE reactivities to native purified DerP1.

The DNA code has 4 letters (A, T, C and G) and uses these to spell three letter "codons" which represent the amino acids the proteins encoded in an organism's genes. The linear sequence of codons along the DNA molecule is translated into the linear sequence of amino acids in the protein(s) encoded by those genes. The code is highly degenerate, with 61 codons coding for the 20 natural amino acids and 3 codons representing "stop" signals. Thus, most amino acids are coded for by more than one codon—in fact several are coded for by four or more different codons.

Where more than one codon is available to code for a given amino acid, it has been observed that the codon usage patterns of organisms are highly non-random. Different species show a different bias in their codon selection and, furthermore, utilization of codons may be markedly different in a single species between genes which are expressed at high and low levels. This bias is different in viruses, plants, bacteria, insect and mammalian cells, and some species show a stronger bias away from a random codon selection than others. For example, humans and other mammals are less strongly biased than certain bacteria or viruses. For these reasons, there is a significant probability that a mammalian gene expressed in *E.coli* or a viral gene expressed in mammalian cells will have an inappropriate distribution of codons for efficient expression. However, a gene with a codon usage pattern suitable for *E.coli* expression may also be efficiently expressed in humans. It is believed that the presence in a heterologous DNA sequence of clusters of codons which are rarely observed in the host in which expression is to occur, is predictive of low heterologous expression levels in that host.

There are several examples where changing codons from those which are rare in the host to those which are host-preferred ("codon optimisation") has enhanced heterologous expression levels, for example the BPV (bovine papilloma virus) late genes L1 and L2 have been codon optimised for mammalian codon usage patterns and this has been shown to give increased expression levels over the wild-type HPV sequences in mammalian (Cos-1) cell culture (Zhou et. al. J. Virol 1999. 73, 4972–4982). In this work, every BPV codon which occurred more than twice as frequently in BPV than in mammals (ratio of usage >2), and most codons with a usage ratio of >1.5 were conservatively replaced by the preferentially used mammalian codon. In WO97/31115, WO97/48370 and WO98/34640 (Merck & Co., Inc.) codon optimisation of HIV genes or segments thereof has been shown to result in increased protein expression and improved immunogenicity when the codon optimised sequences are used as DNA vaccines in the host mammal for which the optimisation was tailored. In this work, the sequences consist entirely of optimised codons (except where this would introduce an undesired restriction site, intron splice site etc.) because each viral codon is conservatively replaced with the optimal codon for the intended host.

LEGEND TO FIGURES

FIG. 1. Codon usage of ProDer p 1 and highly expressed human (High) genes.

Codon usage of a synthetic ProDer p 1 gene (synthetic) after optimisation of codon usage is also represented. Percentage frequencies of individual codons are shown for each corresponding amino acid. The most prevalent codon is shown in bold.

FIG. 2. PCR synthesis of ProDer p 1 cDNA.

A set of 14 mutually priming oligonucleotides were used for PCR amplification of a synthetic ProDer p 1 cDNA. After one round of amplification, amplified products were submitted to a second PCR amplification using external primers (primers 1 and 14). Oligonucleotides which served as PCR templates for the synthesis are represented by solid bars. Unique restriction sites into the synthetic Proder p 1 cDNA which were used for the cloning into the eukaryotic pEE 14 expression vector are shown above. After each of the two rounds of PCR amplification, electrophoresis on agarose gel of the amplified fragments are also shown.

Figure 3:
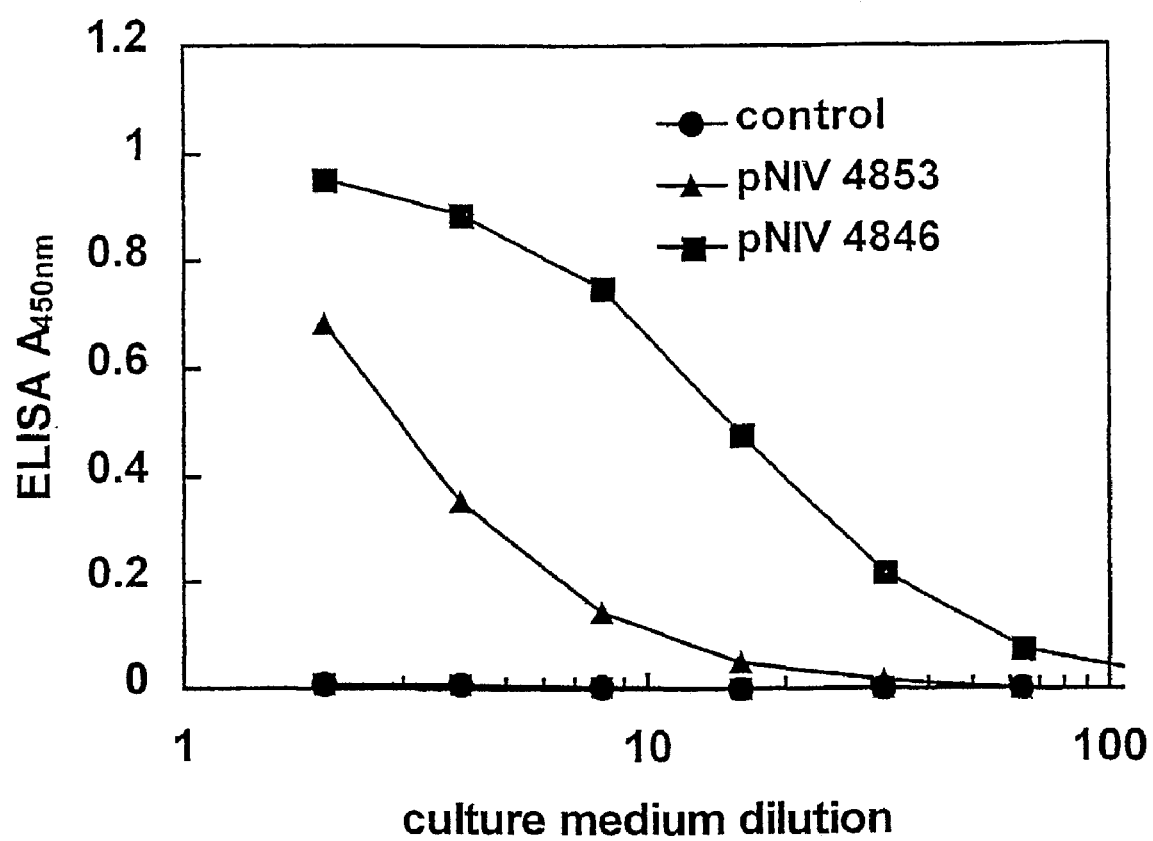

FIG. 3. Expression of synthetic and natural ProDer p 1 in transient transfection assays.

Supernatants from COS cells transfected with plasmids encoding natural (pNIV 4853) or synthetic ProDer p 1 (pNIV 4846) were assayed for the presence of secreted recProDer p 1 in a Der p 1 ELISA. Supernatant from COS transfected with a plasmid without insert was used as control.

FIG. 4. Purification of recProDer p 1.

Purified allergens were analyzed by SDS-PAGE and proteins were detected by Coomassie blue staining (panel A), by immunoblotting with rabbit polyclonal serum raised against Der p 1 peptide 245–267 (panel B). Lane 1: purified recProDer p 1. Lane 2: purified Der p 1

Figure 5:
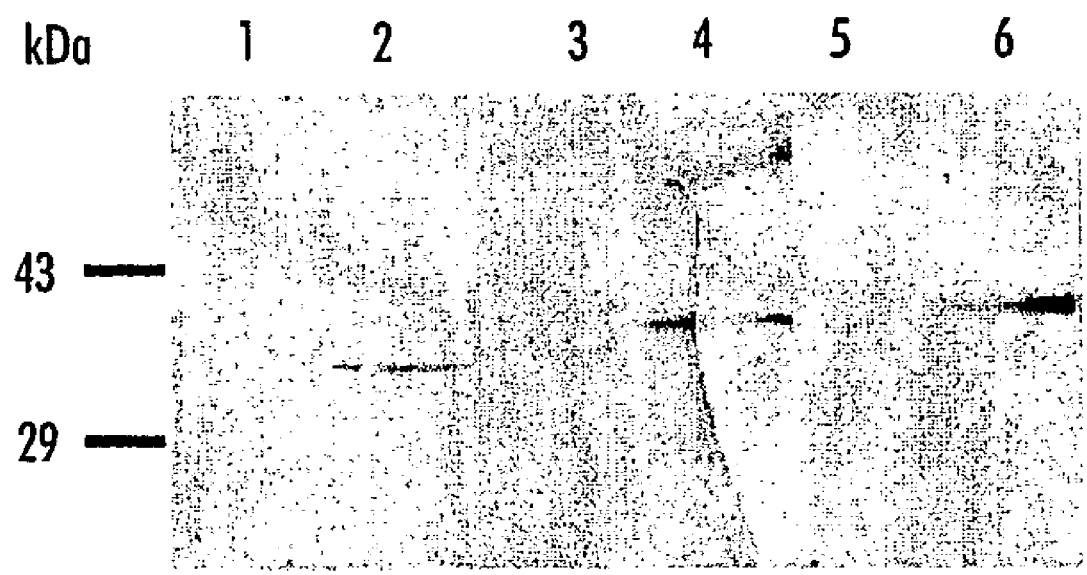

FIG. 5. Carbohydrate analysis of recProDer p 1.

Glycosylations of purified allergens were analysed by lectin staining with *Galanthus nivalis* agglutinin (GNA, Lane 1, 2), *Datura stramonium* agglutinin (DSA, Lane 3, 4) and *Maackia amurensis* agglutinin (MAA, Lane 5, 6). Lane 1, 3, 5: purified Der p 1. Lane 2, 4, 6: purified recProDer p 1

Figure 6:
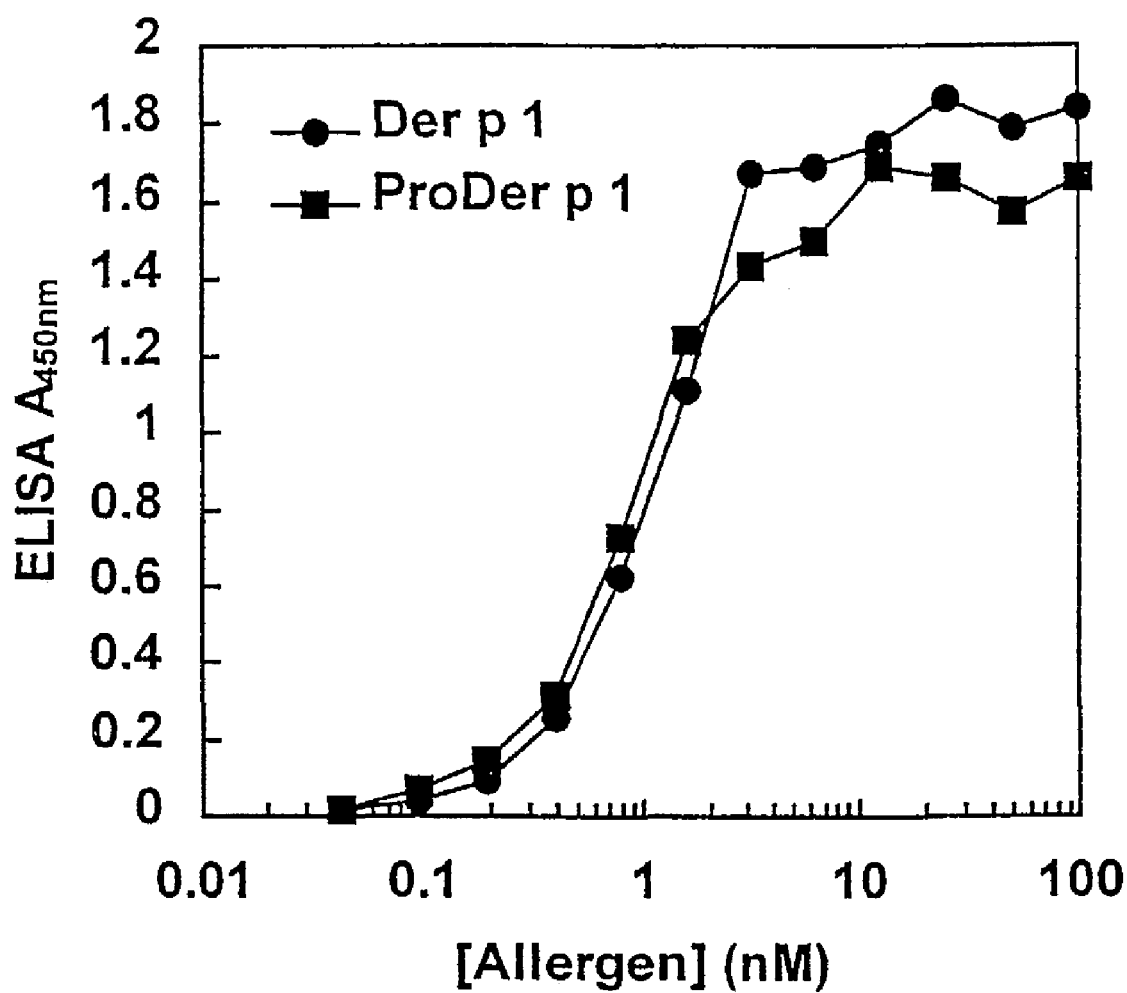

FIG. 6. Immune recognition of recProDer p 1 by monoclonal antibodies directed to Der p 1.

Reactivity of Der p 1 (●) and recProDer p 1 (■) towards monoclonal antibodies was assayed in a two-site ELISA. Both allergens were used at the same concentration which was determined in a total protein assay (MicroBCA, Pierce).

Figure 7:
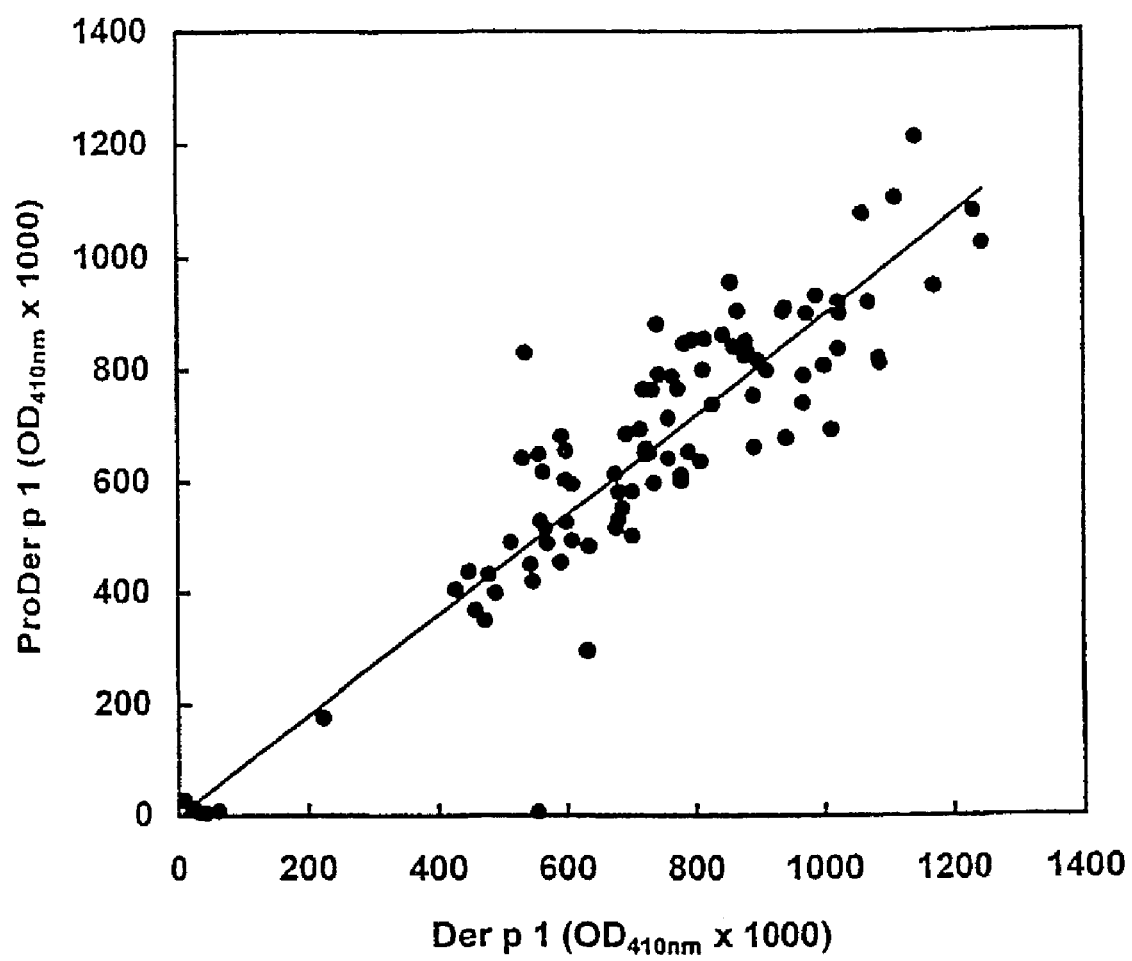

FIG. 7. Correlation between the IgE reactivity of recProDer p 1 and Der p 1.

Immunoplates were coated with 500 ng/well of purified Der p 1 or recProDer p 1 and incubated with 95 sera (diluted 1:8) radioallergosorbent positive to *D.pteronyssinus*. Bound IgE was quantitated by incubation with mouse anti-human IgE and alkaline phosphatase-labelled anti-mouse IgG antibodies, followed by an enzymatic assay. Results are expressed as $OD_{410\ nm}$ values.

Figure 8:
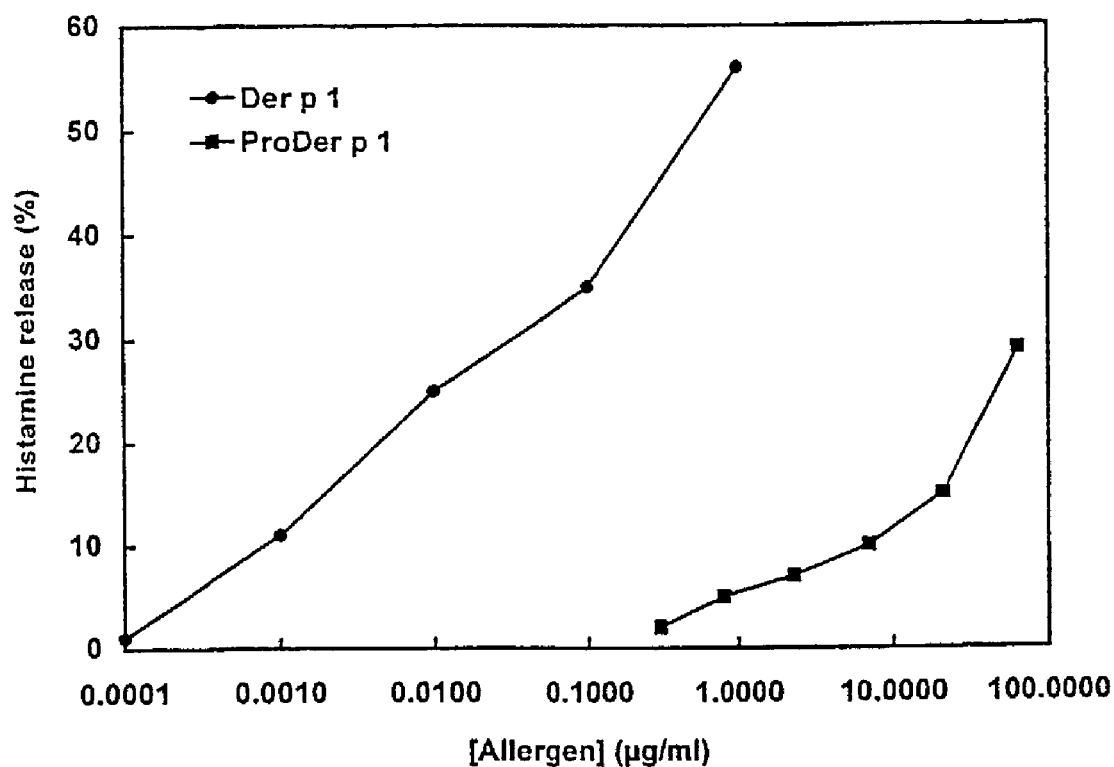

FIG. 8. Histamine release activity of recProDer p 1

Basophils isolated from the peripheral blood of one allergic donor were stimulated with serial dilutions of natural Der p 1 (●) or recProDer p 1 (■). The histamine released from cells was measured by ELISA. The total amount of histamine in basophils was quantified after cell disruption with the detergent IGEPAL CA-630. Results are shown as the ratio of released histamine by allergens to total histamine.

SUMMARY OF THE INVENTION

According to a first aspect, the present invention provides a polynucleotide sequence which encodes a *Dermatophagoides* mite protein, wherein the codon usage pattern of the polynucleotide sequence resembles that of highly expressed mammalian genes.

Preferably the polynucleotide sequence is a DNA sequence. Desirably the codon usage pattern of the polynucleotide sequence is typical of highly expressed human genes. Preferably the house dust mite protein in all of the following aspects of the present invention is derived from *Dermatophagoides pteronyssinus* or *Dermatophagoides farinae*. Most preferably, the *Dermatophagoides pteronyssinus* protein is DerP1 or ProDerP1 or DerP2.

Accordingly there is provided in a first aspect of the present invention, a synthetic gene comprising a plurality of codons together encoding a *Dermatophagoides* protein; wherein the selection of the possible codons used for encoding the recombinant insect protein amino acid sequence has been changed to closely mimic the optimised mammalian codon usage, such that the frequency of codon usage in the synthetic gene is substantially the same as a mammalian gene which encodes the same protein.

Preferably in this first aspect, all of the amino acid types present in the protein are optimised such that the codons used to encode that amino acid are used in the same frequency as the known mammalian frequency for that amino acid. In addition, in preferred optimised codon synthetic genes are used in expression systems that have a protein yield which is greater than 20% higher, and more preferably greater than 50% and most preferably more than 100% higher in yield than the amount of protein produced from the same expression system using a non-optimised native gene for that *Dermatophagoides* protein.

Alternatively, in a second aspect of the present invention there is provided an isolated nucleic acid molecule encoding an *Dermaphagoides* protein, characterised in that the codons present in said polynucleotide which are used to encode each amino acid are selected to appear in substantially the same frequency as set forth in table 1.

TABLE 1

| Codon usage frequency in mammalian cells | | | | | |
|---|---|---|---|---|---|
| Amino Acid | Codon | Frequency (percentage used) | Amino Acid | Codon | Frequency (percentage used) |
| Ala | GCG | 17 | Ile | ATA | 5 |
|  | GCA | 13 |  | ATT | 18 |
|  | GCT | 17 |  | ATC | 77 |
|  | GCC | 53 |  |  |  |
| Arg | AGG | 18 | Leu | TTG | 6 |
|  | AGA | 10 |  | TTA | 2 |
|  | CGG | 21 |  | CTG | 58 |
|  | CGA | 6 |  | CTA | 3 |
|  | CGT | 7 |  | CTT | 5 |
|  | CGC | 37 |  | CTC | 26 |
| Asn | AAT | 22 | Lys | AAG | 82 |
|  | AAC | 78 |  | AAA | 18 |
| Asp | GAT | 25 | Phe | TTT | 20 |
|  | GAC | 75 |  | TTC | 80 |
| Cys | TGT | 32 | Pro | CCG | 17 |
|  | TGC | 68 |  | CCA | 16 |
|  |  |  |  | CCT | 19 |
|  |  |  |  | CCC | 48 |
| Gln | CAG | 88 | Ser | AGT | 10 |
|  | CAA | 12 |  | AGC | 34 |
|  |  |  |  | TCG | 9 |
|  |  |  |  | TCA | 5 |
|  |  |  |  | TCT | 13 |
|  |  |  |  | TCC | 28 |
| Glu | GAG | 75 | Thr | ACG | 15 |
|  | GAA | 25 |  | ACA | 14 |
|  |  |  |  | ACT | 14 |
|  |  |  |  | ACC | 57 |
| Gly | GGG | 24 | Tyr | TAT | 26 |
|  | GGA | 14 |  | TAC | 74 |
|  | GGT | 12 |  |  |  |
|  | GGC | 50 |  |  |  |
| His | CAT | 21 | Val | GTG | 64 |
|  | CAC | 79 |  | GTA | 5 |
|  |  |  |  | GTT | 7 |
|  |  |  |  | GTC | 25 |

In this context, the meaning of "substantially" is intended to mean that the percentage usage of a particular codon is the figure as appearing in the table ±20%, more preferably ±15%, more preferably ±10%, and ideally ±5%.

Alternatively, in a third aspect of the present invention there is provided, a synthetic gene comprising a plurality of codons together encoding a *Dermatophagoides* protein, characterised in that each type of amino acid type has a $\chi^2$ value which is not significantly different, at a confidence interval of between 80–99%, to the corresponding $\chi^2$ value of that same amino acid type as found in a theoretical mammalian gene; said $\chi^2$ value being calculated using the following formula:

$$\chi_k^2 = \sum \frac{(x_{ij} - x_j/n)^2}{(x_j/n)}$$

wherein $x_{ij}$ is the number of codons of type j in sequence i, n is the total number of codons for a particular amino acid k in the sequence, and $x_j$ is the total number of codons of type j in the 2 sequences. The degrees of freedom of the variable is equal to the number of different possible codons minus 1.

Along these same lines, the present invention can also be expressed as providing a synthetic gene comprising a plurality of codons together encoding a *Dermatophagoides* protein; characterised in that between 60–100% of the different types of amino acids present in the synthetic gene are optimised, characterised in that an amino acid type is considered to be optimised if its $\chi^2$ value in the synthetic gene is less that the Limit $\chi^2$ value for significance (5%), for that particular amino acid as defined in the following table:

| Amino Acid | Limit X² value for significance (5%) |
|---|---|
| Ala | 7.81 |
| Cys | 3.84 |
| Asp | 3.84 |
| Glu | 3.84 |
| Phe | 3.84 |
| Gly | 7.81 |
| His | 3.84 |
| Ile | 5.99 |
| Lys | 3.84 |
| Leu | 11.1 |
| Asn | 3.84 |
| Pro | 7.81 |
| Gln | 3.84 |
| Arg | 11.1 |
| Ser | 11.1 |
| Thr | 7.81 |
| Val | 7.81 |
| Tyr | 3.84 | said $\chi^2$ value being calculated using the following formula:

$$\chi_k^2 = \sum \frac{(x_{ij} - x_j/n)^2}{(x_j/n)}$$

wherein $x_{ij}$ is the number of codons of type j in sequence i, n is the total number of codons for a particular amino acid k in the sequence, and $x_j$ is the total number of codons of type j in the 2 sequences. The degrees of freedom of the variable is equal to the number of different possible codons minus 1. Preferably, more than 70% of the amino acids are optimised, more preferably more than 80% are optimised and most preferably greater than 90% of the codons are optimised.

Surprisingly such optimised *Dermatophagoides* genes express very well in mammalian cells such as CHO cells, but also express very well in yeast cells despite the different codon usage of yeast.

The present invention also provides an expression vector is provided which comprises, and is capable of directing the expression of, a polynucleotide sequence according to the first to third aspects of the invention, encoding a *Dermatophagoides* amino acid sequence wherein the codon usage pattern of the polynucleotide sequence is typical of highly expressed mammalian genes, preferably highly expressed human genes. The vector may be suitable for driving expression of heterologous DNA in bacterial insect or mammalian cells, particularly human cells.

Host cells comprising a polynucleotide sequence according to the first aspect of the invention, or an expression vector according the second aspect, is provided. The host cell may be bacterial, e.g. *E.coli*; mammalian, e.g. human; or may be an insect cell. Mammalian cells comprising a vector according to the present invention may be cultured cells transfected in vitro or may be transfected in vivo by administration of the vector to the mammal.

Pharmaceutical compositions comprising a recombinant *Dermatophagoides* protein expressed by the polynucleotides of the present invention, or the codon optimised polynucleotide sequences are also provided.

Preferably the pharmaceutical compositions comprises a DNA vector according to the second aspect of the present invention. In preferred embodiments the composition comprises a plurality of particles, preferably gold particles, coated with DNA comprising a vector encoding a polynucleotide sequence which encodes a *Dermatophagoides* amino acid sequence, wherein the codon usage pattern of the polynucleotide sequence is typical of highly expressed mammalian genes, particularly human genes. In alternative embodiments, the composition comprises a pharmaceutically acceptable excipient and a DNA vector according to the second aspect of the present invention. The composition may also include an adjuvant.

In a further aspect, the present invention provides a method of making a pharmaceutical composition including the step of altering the codon usage pattern of a wild-type *Dermatophagoides* nucleotide sequence, or creating a polynucleotide sequence synthetically, to produce a sequence having a codon usage pattern typical of highly expressed mammalian genes and encoding a wild-type *Dermatophagoides* amino acid sequence or a mutated *Dermatophagoides* amino acid sequence comprising the wild-type sequence with amino acid changes sufficient to inactivate one or more of the natural functions of the polypeptide. The method further comprising the expression of the synthetic polynucleotide sequence in a mammalian host cell, purification of the expressed recombinant protein, and formulation with pharmaceutically acceptable excipients. Methods of preparing a vaccine are provided when the pharmaceutically acceptable excipients comprises an adjuvant. Adjuvants are well known in the art (Vaccine Design—The Subunit and Adjuvant Approach, 1995, Pharmaceutical Biotechnology, Volume 6, Eds. Powell, M. F., and Newman, M. J., Plenum Press, New York and London, ISBN 0-306-44867-X).

Codon usage patterns for mammals, including humans can be found in the literature (see e.g. Nakamura et.al. Nucleic Acids Research 1996, 24:214–215).

The polynucleotides according to the invention have utility in the production by expression of the encoded proteins, which expression may take place in vitro, in vivo or ex vivo. The nucleotides may therefore be involved in recombinant protein synthesis, for example to increase yields, or indeed may find use as therapeutic agents in their own right, utilised in DNA vaccination techniques. Where the polynucleotides of the present invention are used in the production of the encoded proteins in vitro or ex vivo, cells, for example in cell culture, will be modified to include the polynucleotide to be expressed. Such cells include transient, or preferably stable mammalian cell lines. Particular examples of cells which may be modified by insertion of vectors encoding for a polypeptide according to the invention include mammalian HEK293T, CHO, HeLa, 293 and COS cells. Preferably the cell line selected will be one which is not only stable, but also allows for mature glycosylation and cell surface expression of a polypeptide. Expression may be achieved in transformed oocytes. A polypeptide may be expressed from a polynucleotide of the present invention, in cells of a transgenic non-human animal, preferably a mouse. A transgenic non-human animal expressing a polypeptide from a polynucleotide of the invention is included within the scope of the invention.

Where the polynucleotides of the present invention find use as therapeutic agents, e.g. in DNA vaccination, the nucleic acid will be administered to the mammal e.g. human to be vaccinated. The nucleic acid, such as RNA or DNA, preferably DNA, is provided in the form of a vector, such as those described above, which may be expressed in the cells of the mammal. The polynucleotides may be administered by any available technique. For example, the nucleic acid may be introduced by needle injection, preferably intradermally, subcutaneously or intramuscularly. Alternatively, the nucleic acid may be delivered directly into the skin using a nucleic acid delivery device such as particle-mediated DNA delivery (PMDD). In this method, inert particles (such as gold beads) are coated with a nucleic acid, and are accelerated at speeds sufficient to enable them to penetrate a surface of a recipient (e.g. skin), for example by means of discharge under high pressure from a projecting device. (Particles coated with a nucleic acid molecule of the present invention are within the scope of the present invention, as are delivery devices loaded with such particles).

Suitable techniques for introducing the naked polynucleotide or vector into a patient include topical application with an appropriate vehicle. The nucleic acid may be administered topically to the skin, or to mucosal surfaces for example by intranasal, oral, intravaginal or intrarectal administration. The naked polynucleotide or vector may be present together with a pharmaceutically acceptable excipient, such as phosphate buffered saline (PBS). DNA uptake may be further facilitated by use of facilitating agents such as bupivacaine, either separately or included in the DNA formulation. Other methods of administering the nucleic acid directly to a recipient include ultrasound, electrical stimulation, electroporation and microseeding which is described in U.S. Pat. No. 5,697,901.

Uptake of nucleic acid constructs may be enhanced by several known transfection techniques, for example those including the use of transfection agents. Examples of these agents includes cationic agents, for example, calcium phosphate and DEAE-Dextran and lipofectants, for example, lipofectam and transfectam. The dosage of the nucleic acid to be administered can be altered. Typically the nucleic acid is administered in an amount in the range of 1 pg to 1 mg, preferably 1 pg to 10 µg nucleic acid for particle mediated gene delivery and 10 µg to 1 mg for other routes.

A nucleic acid sequence of the present invention may also be administered by means of specialised delivery vectors useful in gene therapy. Gene therapy approaches are discussed for example by Verme et al, Nature 1997, 389: 239–242. Both viral and non-viral vector systems can be used. Viral based systems include retroviral, lentiviral, adenoviral, adeno-associated viral, herpes viral, Canarypox and vaccinia-viral based systems. Non-viral based systems include direct administration of nucleic acids, microsphere encapsulation technology (poly(lactide-co-glycolide) and, liposome-based systems. Viral and non-viral delivery systems may be combined where it is desirable to provide booster injections after an initial vaccination, for example an initial "prime" DNA vaccination using a non-viral vector such as a plasmid followed by one or more "boost" vaccinations using a viral vector or non-viral based system.

A nucleic acid sequence of the present invention may also be administered by means of transformed cells. Such cells include cells harvested from a subject. The naked polynucleotide or vector of the present invention can be introduced into such cells in vitro and the transformed cells can later be returned to the subject. The polynucleotide of the invention may integrate into nucleic acid already present in a cell by homologous recombination events. A transformed cell may, if desired, be grown up in vitro and one or more of the resultant cells may be used in the present invention. Cells can be provided at an appropriate site in a patient by known surgical or microsurgical techniques (e.g. grafting, microinjection, etc.)

The pharmaceutical compositions of the present invention may include adjuvant compounds, or other substances which may serve to increase the immune response induced by the protein which is encoded by the DNA. These may be encoded by the DNA, either separately from or as a fusion with the antigen, or may be included as non-DNA elements of the formulation. Examples of adjuvant-type substances which may be included in the formulations of the present invention include ubiquitin, lysosomal associated membrane protein (LAMP), hepatitis B virus core antigen, FLT3-ligand (a cytokine important in the generation of professional antigen presenting cells, particularly dentritic cells) and other cytokines such as IFN-γ and GMCSF.

Examples of other mite allergens that may be codon optimised according to the methods of the present invention are DerF3 and DP15. DerE3 is a serine protease from *Dermatophagoides farinae* (accession D63858NID/g1311456). DP15 is major allergen p Dp 15=glutathione S-transferase homolog from *Dermatophagoides pteronyssinus* (accession S75286/g807137).

The codon usage pattern of DerF3 and DP15 are shown in the following table:

| | $X^2$ value of native DerF3 | $X^2$ value of native DP15 | Limit $X^2$ value for significance (5%) |
|---|---|---|---|
| Ala | 10.6 | 3.4 | 7.81 |
| Cys | 4.7 | 0.5 | 3.84 |
| Asp | 17.5 | 8.0 | 3.84 |
| Glu | 11.5 | 8.2 | 3.84 |
| Phe | 4 | 4.7 | 3.84 |
| Gly | 25.7 | 11.3 | 7.81 |
| His | 9.6 | 3.0 | 3.84 |
| Ile | 16.0 | 8.9 | 5.99 |
| Lys | 14.6 | 10.2 | 3.84 |

-continued

| | $X^2$ value of native DerF3 | $X^2$ value of native DP15 | Limit $X^2$ value for significance (5%) |
|---|---|---|---|
| Leu | 22.4 | 12.7 | 11.1 |
| Asn | 9.9 | 15.2 | 3.84 |
| Pro | 9.4 | 6.3 | 7.81 |
| Gln | 16.1 | 10.9 | 3.84 |
| Arg | 12 | 13.7 | 11.1 |
| Ser | 21.1 | 4.3 | 11.1 |
| Thr | 7.3 | 3.0 | 7.81 |
| Val | 19 | 5.9 | 7.81 |
| Tyr | 9.2 | 12.7 | 3.84 |

Values in bold are statistically significant (amino acids that are not codon optimised)

Optimised genes may be designed using a Visual Basic program called Calcgene, written by R. S. Hale and G Thompson (Protein Expression and Purification Vol. 12 pp. 185–188 (1998)). For each amino acid residue in the original sequence, a codon was assigned based on the probability of it appearing in highly expressed mammalian or human genes. Details of the program, which works under Microsoft Windows 3.1, can be obtained from the authors. In this article, certain rare codons were excluded from the optimisation process to obviate the possibility of generating clusters of rare codons together which would otherwise prejudice the efficient expression of the gene. In the context of this invention, therefore, either the man skilled in the art can visually check the sequence of the polynucleotide to verify that no clusters of rare codons were present in the optimised gene, or alternatively, one or more rare codons may be excluded from the optimisation process.

REFERENCES

1. Platt-Mills and Chapman, J Allergy Clin Immunol 1987; 80:755–775.
2. Chapman et al., J Allergy Clin Immunol 1983;72: 27–33.
3. Krillis et al., J Allergy Clin Immunol 1984;74:132–141.
4. Shakib et al., Immunol Today 1998;19:313–316.
5. Gouch et al., J Exp Med 1999;12:1897–1901.
6. Chua Ket al., J Exp Med 1988;167:175–182.
7. Chua et al., Int Arch Allergy Immunol 1993;101:364–368.
8. Chapman and Platts-Mills, J Immunol 1980;125:587–592.
9. Chapman et al., Int Arch Allergy Immunol 1997;113: 102–104.
10. Greene et al., J Immunol 1991;147:3768–3773.
11. Chua et al., J Allergy Clin Immunol 1992;89:95–102.
12. Scobie et al., Biochem Soc Trans 1994;22:448S
13. Jacquet et al., Clin Exp Allergy 2000;30:677–684.
14. Sharp and Li, Nucleic Acids Res 1987;15:1281–1295.
15. Cherry M: Codon usage and frequency of codon occurrence, In Ausubel F M, Brent R, Kingston R E, Moore D D, Seidman J G, Smith J A, Struhl K (ed.), Current protocols in molecular biology. John Wiley & Sons, Inc., New York, N.Y., 1992, p. A1.8–A1.9.
16. Cockett et al.,. Biotechnology 1990;8:662–667
17. Jeannin et al., Mol Immunol 1993;30:1511–18.
18. Palermo et al., J Biotechnol 1991;19:35–47.
19. Chambers et al., Biochem Soc Trans 1997;25:85S.
20. Schulz et al., Mol Pathol 1998;51:222–224.
21. Hauser H: Heterologous expression of genes in mammalian cells. in Hauser H, Wagner R ed, Mammalian cell biotechnology in protein production. De Gruyter, Berlin, New-York, 1997, p 1–27
22. Holm L, Nucleic Acids Res 1986;14:3075–3087.
23. Haas et al., Current Biology 1996;6:315–324.
24. Zhou et al., J Virol 1999;73:4972–4982.
25. zur Megede et al.,. J Virol 2000;74:2628–2635.
26. Smith D, Biotechnol Prog 1996;12:417–422.
27. Kleber-Janke and Becker, Prot Expr Purif 2000;19: 419–424.
28. Vailes et al., Proceedings of the XVIIth International Congress of Allergology and Clinical Immunology, Sidney, 2000.
29. Bond et al., Mol Immunol 1993;30:1529–1541.
30. Takahashi et al., Int Arch Allergy Immunol 2000;122: 108–114.
31. Mita et al., Clin Exp Allergy 2000;30:1582–1590.

The present invention is exemplified but not limited to the following examples.

EXAMPLE 1

Expression of RecProDerP1 in COS and CHO Cells

Construction of ProDer p 1 Synthetic Gene

A "humanised" ProDer p 1 gene was synthetised using a set of 14 partially overlapping oligonucleotides. These primers were designed, based on the codon usage of highly expressed human genes, and produced by an 394 DNA/RNA Applied Biosystem synthetizer The degenerately encoded amino acids were not encoded by the most prevalent codons but taking the frequencies of the individual codons into account. For example, histidine residue is encoded by CAC or CAT with a respective frequency of 79% and 21% in highly expressed human genes. Consequently, we attempted to follow the same codon frequency instead of selecting only the CAC codon for each histidine residue in the synthetic ProDer p 1. The native Der p 1 signal sequence was exchanged with the highly efficient leader peptide of the VZV glycoprotein E (gE) to facilitate secretion. The oligonucleotides were the following:

SEQ ID NO.1
5'GAAGCTTCGGGCGAATTGCGTGGTTTTAAGTGACTATATTCGAGGGTC
GCCTGTAATATGGGGACAGTTAATAAACCTGTGGTGGGGTATTGATGGG
GTTCGGAATTATCACG3' (oligo 1, coding);

SEQ ID NO.2
5'GAAGGCTTTCTTGTATTCCTCGAAGGTCTTAATGGAGCTCGGCCGTGC
TCTGACCGGATTCGTTATACGC AAGGTACCCGTGATAATTCCGAACCC
3' (oligo2, non coding);

SEQ ID NO.3
5'GGAATACAAGAAAGCCTTCAACAAGAGCTATGCCACCTTCGAGGACGA
GGAGGCCGCGCGCAAGAACTTCCTGGAAAGCGTGAAATACGTGCAGAGC3'
(oligo 3, coding);

SEQ ID NO.4
5'GTCTTAAGGTGTTCGAAAGCCTCGGCGCTCATCAGGAACCGGTTCTT
GAACTCGTCTAAAGACAGGTCGGACAGGTGATTTATAGCCCCGCCGTT
GCTCTGCACGTATTTCAC3' (oligo 4, non coding);

SEQ ID NO.5
5'CTTTCGAACACCTTAAGACCCAGTTTGATCTCAACGCGGAGACCAACG
CCTGCAGTATCAACGG CAATGCCCCCGCTGAGATTGATCTGCGCC3'
(oligo 5, coding);

SEQ ID NO.6
5'GACTCTGTCGCGGCCACGCCTGAAAAGGCCCAACAAGACCCGCAGCCG
CCTTGCATGCGGATGGGAGTCACGGTCCTCATCTGGCGCAGATCAATCTCA
G3' (oligo 6, non coding);

-continued

SEQ ID NO.7
5'GTGGCCGCGACAGAGTCGGCATACCTCGCGTATCGGAATCAGAGCCTG
GACCTCGCTGAGCAGGAGCTCGTTGACTGCGCCTCCCAAC ACGG3'
(oligo 7, coding);

SEQ ID NO.8
5'GCTACGTATCGGTAATAGCTTTCCTGCACGACGCCATTATGCTGGATG
TATTCGATACCTCTGGGAATCGTATC-
CCCATGACATCCGTGTTGGGAGGCGC3'
(oligo 8, non coding);

SEQ ID NO.9
5'GCTATTACCGATACGTAGCTAGGGAGCAGTCCTGCCGCCGTCCTAACG
CACAGCGCTTCG GCATTTCCAATTATTGCCAGATCTACC3'
(oligo 9, coding);

SEQ ID NO.10
5'CCTTGATTCCGATGATGACAGCGATGGCGCTGTGCGTCTGCGCCAGGG
CCTCCCTGATCTTGTTGGCATTAGGGGGGTAGATCTGGCAATAATTG3'
(oligo 10, non coding);

SEQ ID NO.11
5'GTCATCATCGGAATCAAGGATCTGGACGCATTCCGGCACTATGACGGG
CGCACAATCATCCAGCGCGACAACGGATATCAGCCAAACTACC3'
(oligo 11, coding);

SEQ ID NO.12
5'GTAGTCCACCCCCTGGGCGTTCGAGTAACCCACGATGTTGACCGCGTG
GTAGTTTGGCTGATATCC3' (oligo 12, non coding);

SEQ ID NO.13
5'CCAGGGGGTGGACTACTGGATCGTGAGAAACAGTTGGGACACTAACTG
GGGCGACAACGGCTACGGCTACTTCGCCGCCAAC3'
(oligo 13, coding);

SEQ ID NO.14
5'GCTCTAGACTCGAGGGATCCTTACAGGATCACCACGTACGGGTACTCC
GATCATCATCAGGTCGATGTTGGCGGCGAAGTAGC3'
(oligo 14, non coding).

The oligonucleotides were incubated together for the amplification of a synthetic ProDer p 1 gene in a PCR reaction. Typically, PCR was conducted using High Fidelity Polymerase (Boehringer) with the following conditions: 30 cycles, denaturation at 94° C. for 30 s, annealing at 50° C. for 30 s and elongation at 72° C. for 30 s. The generated products were amplified using the 3' and 5' terminal primers (oligo 1 and 14) in the same conditions. The resulting 1080 bp fragment was cloned into a pCRII-TOPO cloning vector (Invitrogen). The resulting plasmid pNIV4845 was used to transform the E.coli strain TOP 10 (Invitrogen).

The sequences of the natural and codon-optimised genes, together with the encoded amino acid sequence are listed below and are SEQ ID NO.s 15, 16, and 17 respectively. The sequences encode the full ProDerP1, and the nucleic acid or amino acid which is underlined indicates the start of the mature DerP1 sequence resulting from the cleavage of the Pro region.

Natural gene, SEQ ID NO.15
CGTCCATCATCGATCAAAACTTTTGAAGAATACAAAAAAGCCTTCAACAA

AAGTTATGCTACCTTCGAAGATGAAGAAGCTGCCCGTAAAAACTTTTTGG

AATCAGTAAAATATGTTCAATCAAATGGAGGTGCCATCAACCATTTGTCC

GATTTGTCGTTGGATGAATTCAAAAACCGATTTTTGATGAGTGCAGAAGC

TTTTGAACACCTCAAAACTCAATTCGATTTGAATGCTGAAACTAACGCCT

GCAGTATCAATGGAAATGCTCCAGCTGAAATCGATTTGCGACAAATGCGA

ACTGTCACTCCCATTCGTATGCAAGGAGGCTGTGGTTCATGTTGGGCTTT

-continued

CTCTGGTGTTGCCGCAACTGAATCAGCTTATTTGGCTTACCGTAATCAAT

CATTGGATCTTGCTGAACAAGAATTAGTCGATTGTGCTTCCCAACACGGT

TGTCATGGTGATACCATTCCACGTGGTATTGAATACATCCAACATAATGG

TGTCGTCCAAGAAAGCTACTATCGATACGTTGCACGAGAACAATCATGCC

GACGACCAAATGCACAACGTTTCGGTATCTCAAACTATTGCCAAATTTAC

CCACCAAATGTAAACAAAATTCGTGAAGCTTTGGCTCAAACCCACAGCGC

TATTGCCGTCATTATTGGCATCAAAGATTTAGACGCATTCCGTCATTATG

ATGGCCGAACAATCATTCAACGCGATAATGGTTACCAACCAAACTATCAC

GCTGTCAACATTGTTGGTTACAGTAACGCACAAGGTGTCGATTATTGGAT

CGTACGAAACAGTTGGGATACCAATTGGGGTGATAATGGTTACGGTTATT

TTGCTGCCAACATCGATTTGATGATGATTGAAGAATATCCATATGTTGTC

ATTCTCTAA

Synthetic gene, SEQ ID NO 16
CGGCCGAGCTCCATTAAGACCTTCGAGGAATACAAGAAAGCCTTCAACAA

GAGCTATGCCACCTTCGAGGACGAGGAGGCCGCGCGCAAGAACTTCCTGG

AAAGCGTGAAATACGTGCAGAGCAACGGCGGGGCTATAAATCACCTGTCC

GACCTGTCTTTAGACGAGTTCAAGAACCGGTTCCTGATGAGCGCCGAGGC

TTTCGAACACCTTAAGACCCAGTTTGATCTCAACGCGGAGACCAACGCCT

GCAGTATCAACGGCAATGCCCCCGCTGAGATTGATCTGCGCCAGATGAGG

ACCGTGACTCCCATCCGCATGCAAGGCGGCTGCGGGTCTTGTTGGGCCTT

TTCAGGCGTGGCCGCGACAGAGTCGGCATACCTCGCGTATCGGAATCAGA

GCCTGGACCTCGCTGAGCAGGAGCTCGTTGACTGCGCCTCCCAACACGGA

TGTCATGGGGATACGATTCCCAGAGGTATCGAATACATCCAGCATAATGG

CGTCGTGCAGGAAAGCTATTACCGATACGTAGCTAGGGAGCAGTCCTGCC

GCCGTCCTAACGCACAGCGCTTCGGCATTTCCAATTATTGCCAGATCTAC

CCCCCTAATGCCAACAAGATCAGGGAGGCCCTGGCGCAGACGCACAGCGC

CATCGCTGTCATCATCGGAATCAAGGATCTGGACGCATTCCGGCACTATG

ACGGGCGCACAATCATCCAGCGCGACAACGGATATCAGCCAAACTACCAC

GCGGTCAACATCGTGGGTTACTCGAACGCCCAGGGGGTGGACTACTGGAT

CGTGAGAAACAGTTGGGACACTAACTGGGGCGACAACGGCTACGGCTACT

TCGCCGCCAACATCGACCTGATGATGATCGAGGAGTACCCGTACGTGGTG

ATCCTGTAA protein sequence, SEQ ID NO.17
RPSSIKTFEEYKKAF-
NKSYATFEDEE-
AARKNFLESVKYVQSNG-
GAINHLS

DLSLDEFKNRFLMSAEAFE-
HLKTQFDLNAE
TNACSINGNAPAEIDLRQMR

TVTPIRMQGGCGSCWAFS-
GVAATESAYLAYRNQSLD-
LAEQELVDCASQHG

CHGDTIPRGIEYIQHNGV-
VQESYYRYVAREQSCRRP-
NAQRFGISNYCQIY

-continued

PPNANKIREALAQTHSALA-
VIIGIKDLDAFRHYDGRTI-
IQRDNGYQPNYH

AVNIVGYSNAQGVDY-
WIVRNSWDTNWGDNGYGY-
FAANIDLMMIEEYPYVV

IL

Construction of Humanized ProDerp 1 Expression Vector.

As the sequencing of eight bacterial clones demonstrated some mutations in the synthetic ProDer p 1 gene, the plasmid for stable expression was generated starting from four ProDer p 1 DNA fragments derived from bacterial clones carrying pNIV4845. Clones n°5 and n°20 were respectively submitted to double digestions by HindIII-BssHII and SphI-BglII, to isolate the 228 bp HindIII-BssHII and 272 bp SphI-BglII ProDer p 1 DNA fragments. Clone n°o7 was restricted with BssHII-SphI and BglII-XbaI to generate the 239 bp BssHII-SphI and 329 bp BglII-XbaI ProDer p 1 DNA fragments. These fragments were inserted into the HindIII-XbaI cut pEE14 expression vector (Celltech) [16] to give the final plasmid pNIV4846. The correct recombinants were confirmed by DNA sequencing.

Transient Transfections and Selection of recProDer p 1-producing Stable CHO-K1 Lines.

To determine the expression levels of recProDer p 1, COS cells (ATCC) were transiently transfected with 10 µg of pNIV4846 or pNIV4853, a plasmid carrying authentic ProDer p 1 gene, by calcium phosphate coprecipitation. For stable recProDer p 1 expression, CHO-K1 cells (ATCC) were transfected with pNIV4846 plasmid by lipofection. After a 3-weeks 25 µM methionylsulphoximin (MSX, Sigma) selection, one round of gene amplification was carried out with 100 µM MSX.

Expression of the Recombinant Allergen in CHO Cells.

The best producing recombinant CHO-K1 clone was cultured in cell factories in GMEM medium (Invitrogen) supplemented with 2% fetal calf serum (Gibco). Spent culture medium was harvested every 72 h and stored at −20° C. until purification.

Purification of Natural Der p 1 from Natural Mite Whole Body Extracts.

Purification of natural Der p 1 from whole mite culture was performed as previously described [13]. Briefly, D.pteronyssinus extracts were submitted to $(NH_4)_2SO_4$ precipitation to 60% saturation. The precipitate, collected by ultracentrifugation and resuspended in PBS containing $(NH_4)_2SO_4$ 1M, was applied onto a Resource Phenyl column (Pharmacia) equilibrated in PBS containing $(NH_4)_2SO_4$ 1M. Der p 1 was eluted from the column with water. After the pH and conductivity adjustments of the Der p 1-enriched fractions, the pool was applied onto a Q sepharose fast flow column (Pharmacia) equilibrated in 20 mM Tris-HCl pH 9. Der p 1 was eluted by addition of 200 mM NaCl in the starting buffer. The Der p 1 purification was achieved by a gel filtration chromatography onto a superdex-75 column (Pharmacia) equilibrated in PBS pH 7,3. Purified Der p 1 was concentrated and stored at −20° C.

Purification of recProDer p 1 from CHO Spent Culture Medium.

CHO spent culture medium was diluted two times with water and the pH was adjusted to 7.2. The modified supernatant was loaded onto a Q sepharose fast flow column (5×10 cm, Pharmacia) equilibrated in 20 mM Tris-HCl pH 7.2 which is coupled to a hydroxyapatite column (2.6×15 cm, Bio-Rad) conditioned in the same buffer. The flow-through containing recProDer p 1 of both columns was adjusted to pH 9 and applied onto a Q sepharose fast flow column (1.6×10 cm) equilibrated in 20 mM Tris-HCl pH 9. The column was washed with the starting buffer and with the same buffer supplemented with 100 mM NaCl. ProDer p 1 was eluted by a linear NaCl gradient (100–300 mM, 15 column volumes). The recProDer p 1-enriched fractions were pooled and concentrated by ultrafiltration onto a Filtron membrane (Omega serie, cut-off: 10 kD). The recProDer p 1 purification was achieved by a gel filtration chromatography onto a superdex-75 column (1×30 cm, Pharmacia) equilibrated in PBS pH 7,3. Purified recProDer p 1 was concentrated and stored at −20° C.

SDS PAGE and Western Blot Analysis

Proteins were analyzed by SDS-PAGE on 12.5% polyacrylamide gels. After electrophoresis, proteins were transferred onto nitrocellulose membranes using a semi-dry transblot system (Bio-Rad). Membranes were saturated for 30 min with 0.5% Instagel (PB Gelatins) in TBS-T (50 mM Tris HCl pH 7.5, 150 mM NaCl, 0.1% Tween 80) and incubated with rabbit polyclonal serum raised against Der p 1 peptide 245–267 diluted in blocking solution (1:5000) (Kindly provided by Dr Pestel, Institut Pasteur de Lille, France) [17]. Immunoreactive materials were detected using alkaline phosphatase-conjugated goat anti-rabbit antibodies (Promega, 1:7500) and 5-bromo,4-chloro,3-indolylphosphate (BCIP, Boehringer)/nitroblue tetrazolium (NBT, Sigma) as substrates.

Glycan Analysis

Carbohydrate analysis was carried out with the Glycan Differenciation Kit (Boehringer) using the following lectins: *Galanthus nivalis* agglutinin (GNA), *Sambucus nigra* agglutinin (SNA), *Maackia amurensis* agglutinin (MAA), Peanut agglutinin (PNA) and *Datura strarmonium* agglutinin (DSA). Briefly, purified proteins were transferred from SDS-PAGE onto nitrocellulose membranes. Membranes were incubated with the different lectins conjugated to digoxigenin. Complexes were detected with anti-digoxigenin antibodies conjugated to alkaline phosphatase.

Enzymatic Assays

Enzymatic assays were performed in 50 mM Tris-HCl pH 7, containing 1 mM EDTA and 20 mM L-cysteine at 25° C. in a total volume of 1 ml. Hydrolysis of Cbz-Phe-Arg-7-amino-4-methylcoumarin (Cbz-Phe-Arg-AMC) and Boc-Gln-Ala-Arg-7-amino-4-methylcoumarin (Boe-Gln-Ala-Arg-AMC) (Sigma) (both substrates at a final concentration of 100 µM) was monitored using a SLM 8000 spectrofluorimeter with $\lambda_{ex}$=380 nm and $\lambda_{em}$=460 nm. Assays were started by addition of cysteine activated allergen to a final concentration of 100 nM. Before any assay, purified Der p 1 or recProDer p 1 was incubated with a mixture of aprotinin- and p-aminobenzamidine-agarose resins (Sigma) to remove any putative trace of serine protease activity.

Protein Determination

Total protein concentration was determined by the bicinchoninic acid procedure (MicroBCA, Pierce) with bovine serum albumin as standard.

Der p 1 ELISA

Der p 1 or recProDer p 1 was detected with an ELISA kit using Der p 1 specific monoclonal antibodies 5H8 and 4C1

(Indoor Biotechnologies). The Der p 1 standard (UVA 93/03) used in the assay was at a concentration of 2.5 µg/ml.

IgE-binding Activity.

Immunoplates were coated overnight with Der p 1 or recProDer p 1 (500 ng/well) at 4° C. Plates were then washed 5 times with 100 µl per well of TBS-Tween buffer (50 mM Tris-HCl pH 7.5, 150 mM NaCl, 0.1% Tween 80) and saturated for 1 hr at 37° C. with 150 µl of the same buffer supplemented with 1% BSA (Sigma). Sera from allergic patients to *D. pteronyssinus* and diluted at ⅛ were then incubated for 1 hr at 37° C. Out of the 95 sera used in the experiments, 16 sera ranged in their specific anti-*D.pteronyssinus* IgE values (RAST assays) from 58.1 kU/L to 99 kU/L and 79 above the upper cut-off value of 100 kU/L. Plates were washed 5 times with TBS-Tween buffer and the allergen-IgE complexes were detected after incubation with a mouse anti-human IgE antibody (Southern Biotechnology Associates) and a goat anti-mouse IgG antibody coupled to alkaline phosphatase (dilution 1/7500 in TBS-Tween buffer, Promega). The enzymatic activity was measured using the p-nitrophenylphosphate substrate (Sigma) dissolved in diethanolamine buffer (pH 9.8). $OD_{410\,nm}$ was measured in a Biorad Novapath ELISA reader.

For IgE inhibition assays, plates were coated with Der p 1 or recProDer p 1 at the same concentration (0.12 µM). A pool of 20 human sera from allergic patients (RAST value>100 kU/L) was preincubated overnight at 4° C. with various concentrations (3.6–0.002 µM) of Der p 1 or recProDer p 1 as inhibitors and added on ELISA plates. IgE-binding was detected as described above.

Histamine Release

The histamine release was assayed using leukocytes from the peripheral heparinized blood of an allergic donor and by the Histamine-ELISA kit (Immunotech). Basophils were incubated with serial dilutions of recProDer p 1 or Der p 1 for 30 min at 37° C. The total amount of histamine in basophils was quantified after cell disruption with the detergent IGEPAL CA-630 (Sigma).

Results

Synthesis of Humanized ProDer p 1 Gene.

The codon prevalence of ProDer p 1 gene displayed many divergences compared with that used for highly expressed human genes (FIG. 1). In consequence, oligonucleotides were designed for the construction of a synthetic ProDer p 1 gene to optimise the allergen expression in mammalian cells. As shown in FIG. 1, the final codon frequency in the synthetic ProDer p 1 gene was very similar to that used in highly expressed mammalian genes.

The synthetic ProDer p 1 was assembled from mutually priming oligonucleotides that were subsequently amplified by PCR (FIG. 2). After one round of PCR, amplified products displayed a molecular weight ranging from 3000 to 300 bp. A subsequent amplification with primers complementary to the 5' end of VZV gE leader peptide and to the 3' end of synthetic ProDer p 1 gene led to a 1072 bp fragment of excepted size. The amplified fragment was cloned into the pCRII cloning vector. Sequence analysis of recombinant clones revealed the presence of point mutations and deletions in the synthetic ProDer p 1 gene. Finally, the correct coding cassette was obtained after ligation of 4 different fragments isolated from 3 independent bacterial clones, and inserted in the mammalian expression vector pEE14 to give the final plasmid pNIV4846.

Transient and Stable Expression of recProDer p 1

To compare the expression efficiency of the synthetic ProDer p 1 construct with the original sequence, COS cells were transfected with pNIV4846 and pNIV4853, a pEE14-derived plasmid carrying authentic ProDer p 1 cDNA. The recProDer p 1 expression level of the supernatants was estimated by an ELISA assay, using two anti-Der p 1 monoclonal antibodies. As shown in FIG. 3, the expression vector carrying the synthetic cDNA directed the recProDer p 1 synthesis more efficiently than the same vector containing the authentic gene. The expression level of humanized ProDer p 1 gene was enhanced up to 450 ng/ml/72 h which represents a 6-fold increase compared with the reference construction (75 ng/ml/72 h). As expected, no recProDer p 1 expression was detected using COS cells transfected by a control vector without any insert.

CHO-K1 cells were transfected with pNIV4846 and clones resistant to 25 μM MSX were selected. The recProDer p 1 level assayed by ELISA indicated that three independent clones secreted recProDer p 1 up to 11 μg/ml/72 h. Addition of sodium butyrate, a molecule previously reported to enhance expression level of recombinant proteins in culture medium [18], did not influence the recProDer p 1 synthesis. A further amplification of 25 μM MSX-resistant clones up to 100 μM MSX increased expression, raising 26 to 34 μg/ml/72 h recProDer p 1 in culture medium. The clone n°1 was used for recProDer p 1 large-scale production in cell factories and purification. Spent culture medium was collected every 72 h and up to 9 harvests were performed. In these conditions, the best recProDer p 1 expression level raised 15 μg/ml in the culture medium before purification.

Purifcation of recProDerp 1.

Purification of recProDer p 1 was achieved by a combination of three chromatographic steps, using anion-exchange, hydroxyapatite and gel filtration media. The final purification yield was about 6 mg of recProDer p 1 per litre of culture medium with a recovery close to 40%. On SDS PAGE, purified recProDer p 1 migrated as three immunoreactive species: two major bands with a respective molecular weight of 41 and 36 kD and one minor band of 38 kD (FIG. 4). This result indicated that the propeptide cleavage, to yield mature Der p 1, did not occur during the expression and purification steps, as natural Der p 1 migrated on SDS PAGE as a 29 kD band. The purity of the product was higher than 90%.

Biochemical Characterization of ProDer p 1

All the recProDer p 1 species were submitted to an amino-terminal amino acid sequencing. The N-terminal sequence of 41 and 38 kDa species were identical and started at residue $Arg_{19}$. The sequence was identified as Arg-Pro-Ser-Ser-Ile, which corresponds to the N-terminal sequence of the Der p 1 propeptide and indicates that cleavage of VZV gE signal peptide proceeded efficiently. Surprisingly, the N-terminal sequence of the 36 kDa band started at residue $Ala_{38}$ (the obtained sequence was Ala-Thr-Phe-Glu-Asp) showing that, for the 36 kDa molecule, an internal cleavage of the prosequence occurred between $Tyr_{37}$ and $Ala_{38}$. Carbohydrate analysis of recProDer p 1 was performed by glycan recognition with several specific lectins. Among the five lectins used, only the GNA lectin reacted with the 36 kDa recProDer p 1, pointing to the presence of terminal mannose residues on this molecule, either as high-mannose N-glycan chains or as exposed mannose in hybrid chains (FIG. 5). The 38 and 41 kDa bands were recognized respectively by the DSA and MAA lectins, showing that the 38 kDa molecule carried terminal galactose linked β (1–4) to N-acetyl-glucosamine in N-glycan chains whereas the carbohydrate structure of the upper band was terminated by sialic acid linked α(2–3) to galactose. As previously showed [13], Der p 1 did not react with any lectin confirming that Der p 1 is not glycosylated.

The enzymatic activity of recProDer p 1 was measured using Cbz-Phe-Arg-AMC and Boc-Gln-Ala-Arg-AMC as substrates [19,20]. As expected, because of the presence of the Pro region, RecProDer p 1 was totally inactive in our assays. In the same experimental conditions, fluorogenic molecules were fully degraded within 4 min by natural Der p 1 used at the same molarity.

IgG- and IgE-reactivities of recProDerp 1

RecProDer p 1 was tested in ELISA assays to determine whether the recombinant allergen displayed reactivities similar to those of Der p 1 towards specific anti-Der p 1 IgG and anti-*Dermatophagoides pteronyssinus* IgE. As shown in FIG. 6, equimolar concentrations of both allergens reacted similarly with two Der p 1 specific monoclonal and conformational antibodies, suggesting that recProDer p 1 displayed the overall structure of the natural allergen. The IgE reactivity of recProDer p 1 and Der p 1 was compared in a direct ELISA wherein immunoplates were directly coated with Der p 1 or recProDer p 1. A set of 95 human sera with positive radoimmunosorbent tests to *D. pteronyssinus* extract was used at dilution 1:8. IgE titer determinations clearly showed a close correlation of IgE reactivity with both allergens, indicating that recProDer p 1 has very similar IgE binding characteristics compared with Der p 1 ($R^2$=0.8171, $P<0.0001$) (FIG. 7).

Histamine Releasing Activity of recProDer p 1

To compare the allergenic activity of natural Der p 1 and recProDer p 1, basophils from one allergic patient were challenged in vitro with various concentrations of both allergens and the released histamine was measured. Natural Der p 1 was able to induce histamine release from basophils even at a concentration of 1 ng/ml. By contrast, recProDer p 1 could only release histamine at 1000-fold higher concentration (FIG. 8). From this result, recProDer p 1 was shown to be less allergenic that the natural Der p 1.

EXAMPLE 2

Expression of RecProDerP1 in *Pichia pastoris*

Construction of ProDerp 1 Expression Vector

The ProDer p 1 coding cassette from pNIV4846 (full-length 1-302aa ProDer p 1 cDNA with optimised mammalian codon usage) was amplified by PCR using the following primers: 5'ACTGACAGGCCTCGGCCGAGCTCCATTAA3' (SEQ ID NO. 18) (StuI restriction site in bold, forward) and 5'CAGTCACCTAGGTCTAGACTCGAGGGGAT3' (SEQ ID NO. 19) (AvrII restriction site in bold, reverse). The amplified fragment was cloned into the pCR2.1 TOPO cloning vector. The correct ProDer p 1 cassette was verified by DNA sequencing. Recombinant TOPO vector was digested with StuI-AvrII to generate a 918 bp fragment which was introduced into the pPIC9K expression vector restricted with SnaBI-AvrII. The resulting plasmid, pNIV4878, contains the ProDer p 1 cassette downstream to the *S.cerevisae* α factor.

Site-directed Mutagenesis

Expression plasmid for the production of unglycosylated ProDer p 1 (N52Q, mature Der p 1 numbering) was derived from pNIV4878 by overlap extension PCR using a set of four primers. The following primers: 5'GGCTTTCGAACACCTTAAGACCCAG3' (SEQ ID NO. 20) (primer 1, AflII restriction site in bold, forward) and 5'GCTCCCTAGCTACGTATCGGTAATAGC3' (SEQ ID NO. 21) (primer 2, SnaBI restriction site in bold, reverse) were used to amplify a 317 bp fragment encoding the ProDer p 1 amino acid sequence 71–176. The following primers 5'CCTCGCGTATCGGCAACAGAGCCTGGACC3' (SEQ ID NO. 22) (primer 3, mutation N52Q in bold, forward) and 5'GGTCCAGGCTCTGTTGCCGATACGCGAGG3' (SEQ ID NO. 23) (primer 4, mutation N52Q in bold, reverse) were used to introduce mutation N52Q in the ProDer p 1 sequence.

The mutated 317 bp AflII-SnaBI fragment was generated by a three-step process. In PCR n°1, primers 1 and 4 were mixed with pNIV4878 to produce a ~200bp fragment. In PCR n°2, primers 2 and 3 were mixed with pNIV4878 to produce a ~140bp. The two PCR products were purified onto agarose gel and used as templates for a third round of PCR to obtain a ~340bp fragment. This purified fragment was cloned into the pCR2.1 TOPO cloning vector. The mutation was verified by DNA sequencing. Recombinant TOPO vector was digested with AflII-SnaBI to generate a 317bp fragment which was ligated into the similarly digested pNIV4878. The resulting plasmid, pNIV4883, contains the ProDer p 1 N52Q downstream to the *S.cerevisae* α factor To obtain unglycosylated variants of ProDer p 1 carrying mutations of Der p 1 cysteine residues at position 4, 31 or 65 (mature Der p 1 numbering), overlap extension PCR using the same set of primers were performed with plasmids pNIV4873, pNIV4875 and pNIV4874. The resulting plasmids pNIV4884, 4885 and 4886 encode respectively ProDer p 1 N52Q C4R, N52Q C31R and N52Q C65R.

Transformation of *P.pastoris*

Plasmid pNIV4878 was introduced into *P.pastoris* using the spheroplast transformation method. Transformants were selected for histidinol deshydrogenase (His+) prototrophy. The screening of His+ transformants for geneticin (G418) resistance was performed by plating clones on agar containing increasing concentrations of G418.

Production of ProDerp 1 by Recombinant Yeast

G418 resistant clones were grown at 30° C. in BMG medium to an $OD_{600\ nm}$ of 2–6. Cells were collected by centrifugation and resuspended to an $OD_{600\ nm}$ of 1 in 100 ml of BMG medium. Proder p 1 expression was induced by daily addition of methanol 0.5% for 6 days. The supernatant was collected by centrifugation and stored at −20° C. until purification.

Purification of ProDer p 1 from Yeast Culture Supernatant

Supernatants were diluted 10 times with water and, after pH adjustment to 9, directly loaded onto a Q sepharose column equilibrated in in 20 mM Tris-HCl pH 9. The column was washed with the starting buffer. Protein elutions proceeded by step-wise increasing NaCl concentration in the buffer. The ProDer p 1-enriched fractions were pooled and concentrated by ultrafiltration onto a Filtron membrane (Omega serie, cut-off: 10 kD). The ProDer p 1 purification was achieved by a gel filtration chromatography onto a superdex-75 column (1×30 cm, Pharmacia) equilibrated in PBS pH 7,3. Purified ProDer p 1 was concentrated and stored at −20° C. Surprisingly, given the fact that yeast codon usage is significantly different from the human profile, this humanised ProDerP1 expressed very well in this system with a high yield of protein.

Discussion

The inability to obtain large amounts of Der p 1, the major allergen from *D.pteronyssinus* is a major obstacle for the development of biochemical and immunological studies. Indeed, whole mite culture is cost effective, the growth rate is slow and the purification yield of native Der p 1 is relatively low, about 1 mg Der p 1 being purified from 1 gram of whole mite culture in our experimental conditions. Moreover, previous attempts of Der p 1 expression in bacteria and yeast indicated that the allergen was poorly expressed and mainly under an insoluble form [10–12]. The present study clearly reports that production of recProDer p 1 in mammalian cells is very low indicating that the presence of prosequence is not sufficient to induce high-level recProDer p 1 expression.

The codon prevalence of the Proder p 1 gene was different from that most frequently used in highly expressed human genes. To assess the importance of an appropriate codon usage for the recProDer p 1 expression in CHO cells, we decided to engineer a synthetic ProDer p 1 gene based on the mammalian prevalent codons. Our results clearly demonstrate that codon optimisation is beneficial to induce high-level expression of recProDer p 1 in mammalian cells.

In summary, codon usage optimisation can induces high-level expression of recProDer p 1, an allergen difficult to produce in CHO cells. This strategy could also be applicable for expression of other allergens and could be extrapolate to other expression systems. Synthetic genes with appropriate codons could thus provide new tools for allergy diagnosis and specific immunotherapy.

RecProDer p 1, immobilized on solid phases, could substitute natural Der p 1 in diagnostic test for the detection of specific IgE. Considering the reduced recProDer p 1 anaphylactogenic potential, this recombinant allergen could be used in the future as alternative reagents for immunotherapy to replace the commonly used allergen extracts.

The invention claimed is:

1. An isolated polynucleotide comprising SEQ ID NO: 16.
2. An isolated vector comprising the isolated polynucleotide of claim 1.
3. An isolated host cell comprising the vector of claim 2.
4. A process for producing a polypeptide comprising SEQ ID NO:17, comprising culturing the host cell of claim 3 under conditions sufficient to produce the polypeptide.

* * * * *